United States Patent
Butani et al.

(10) Patent No.: US 11,246,551 B2
(45) Date of Patent: Feb. 15, 2022

(54) SYSTEM AND METHOD FOR COMPUTER AIDED DETECTION (CAD) IN A BREAST SPECIMEN RADIOGRAPH

(71) Applicant: KUB Technologies, Inc., Stratford, CT (US)

(72) Inventors: Vikram Butani, Stratford, CT (US); Yan Chen, Stratford, CT (US); Timothy Ely, Stratford, CT (US); Chester Lowe, Stratford, CT (US); Edwin Maria-Selvaraj, Stratford, CT (US)

(73) Assignee: KUB Technologies, Inc., Stratford, CT (US)

( * ) Notice: Subject to any disclaimer, the term of this patent is extended or adjusted under 35 U.S.C. 154(b) by 494 days.

(21) Appl. No.: 15/709,582

(22) Filed: Sep. 20, 2017

(65) Prior Publication Data

US 2018/0078231 A1 Mar. 22, 2018

Related U.S. Application Data

(60) Provisional application No. 62/396,874, filed on Sep. 20, 2016.

(51) Int. Cl.
*A61B 6/00* (2006.01)
*A61B 6/02* (2006.01)
(Continued)

(52) U.S. Cl.
CPC ............ *A61B 6/5217* (2013.01); *A61B 6/025* (2013.01); *A61B 6/04* (2013.01); *A61B 6/4233* (2013.01);
(Continued)

(58) Field of Classification Search
CPC ..... A61B 6/5217; A61B 6/502; A61B 6/4405; A61B 6/025; A61B 6/54; A61B 6/04;
(Continued)

(56) References Cited

U.S. PATENT DOCUMENTS

| 5,452,367 A | 9/1995 | Bick et al. |
| 5,491,627 A | 2/1996 | Zhang et al. |

(Continued)

OTHER PUBLICATIONS

Giger, MaryEllen, et al., "An 'Intelligent' Workstation for Computer-aided Diagnosis," Radiographics, vol. 13, No. 03, May 1993, pp. 647-656.

(Continued)

*Primary Examiner* — Sean D Mattson
(74) *Attorney, Agent, or Firm* — Ziegler IP Law Group, LLC

(57) ABSTRACT

The present disclosure relates to a system, method, and computer program product for computer-aided detection (CAD) of suspicious lesions in digital breast specimen radiographs, wherein single-view feature vectors from a first digital radiograph of the breast specimen are processed in a classification algorithm along with information computed from a plurality of related digital specimen radiographs to assign an overall probability of suspiciousness to potentially suspicious lesions in the first digital breast specimen radiography. In one embodiment, a greater probability of suspiciousness is determined where there are similar corresponding lesions in the first digital breast specimen radiography and in an alternate digital breast specimen radiography view of the same breast specimen. In another preferred embodiment, a lesser probability of suspiciousness is found where there are symmetric lesions or structures located in the first digital breast specimen radiography and a digital breast specimen radiography of another view.

4 Claims, 14 Drawing Sheets
(10 of 14 Drawing Sheet(s) Filed in Color)

(51) Int. Cl.
*A61B 6/04* (2006.01)
*G06T 7/00* (2017.01)
*G06T 7/11* (2017.01)
*G06T 7/70* (2017.01)

(52) U.S. Cl.
CPC .......... *A61B 6/4291* (2013.01); *A61B 6/4405* (2013.01); *A61B 6/502* (2013.01); *A61B 6/54* (2013.01); *G06T 7/0012* (2013.01); *G06T 7/0014* (2013.01); *G06T 7/11* (2017.01); *G06T 7/70* (2017.01); *G06T 2207/10116* (2013.01); *G06T 2207/30068* (2013.01); *G06T 2207/30096* (2013.01)

(58) Field of Classification Search
CPC ... A61B 6/4291; A61B 6/4233; G06T 7/0014; G06T 7/0012; G06T 7/11; G06T 7/70; G06T 2207/10116; G06T 2207/30069; G06T 2207/30096
See application file for complete search history.

(56) References Cited

U.S. PATENT DOCUMENTS

| | | | |
|---|---|---|---|
| 5,537,485 | A | 7/1996 | Nishikawa et al. |
| 5,572,565 | A | 11/1996 | Abdel-Mottaleb |
| 5,579,360 | A | 11/1996 | Abdel-Mottaleb |
| 5,657,362 | A | 8/1997 | Giger et al. |
| 5,729,620 | A | 3/1998 | Wang |
| 5,815,591 | A | 9/1998 | Roehrig et al. |
| 5,825,910 | A | 10/1998 | Vafai |
| 5,854,851 | A * | 12/1998 | Bamberger ............. G06T 5/008 382/132 |
| 5,917,929 | A | 6/1999 | Marshall et al. |
| 5,941,832 | A | 8/1999 | Tumey et al. |
| 5,982,917 | A | 11/1999 | Clarke et al. |
| 5,999,639 | A | 12/1999 | Rogers et al. |
| 6,075,879 | A | 6/2000 | Roehrig et al. |
| 6,198,838 | B1 | 3/2001 | Roehrig et al. |
| 6,266,435 | B1 | 7/2001 | Wang |
| 6,301,378 | B1 | 10/2001 | Karssemeijer et al. |
| 6,434,262 | B2 | 8/2002 | Wang |
| 6,901,156 | B2 | 5/2005 | Giger et al. |
| 6,956,975 | B2 | 10/2005 | Young |
| 7,885,443 | B2 | 2/2011 | Zingaretti et al. |
| 8,131,049 | B2 * | 3/2012 | Ruth ................... G06K 9/4638 382/131 |
| 8,139,832 | B2 | 3/2012 | Kshirsagar |
| 2005/0113681 | A1* | 5/2005 | DeFreitas ............. A61B 6/502 600/426 |
| 2005/0226369 | A1* | 10/2005 | Martin .................. A61B 6/466 378/22 |
| 2007/0225600 | A1* | 9/2007 | Weibrecht ............. A61B 6/025 600/429 |
| 2008/0021302 | A1 | 1/2008 | Kaiser |
| 2008/0144940 | A1 | 6/2008 | Russakoff |
| 2014/0200433 | A1* | 7/2014 | Choi .................... A61B 5/4887 600/407 |
| 2015/0131773 | A1 | 5/2015 | Lowe et al. |
| 2015/0131778 | A1* | 5/2015 | Lowe .................... A61B 6/502 378/37 |

OTHER PUBLICATIONS

Baker, Jay, et al., "Artificial Neural Network: Improving the Quality of Breast Biopsy Recommendations", Radiology, Jan. 1996, vol. 198, pp. 131-135.
Wu, Yuzheng, et al., "Artificial Neural Networks in Mammography: Application to Decision Making in the Diagnosis of Breast Cancer," Radiology, Apr. 1993, vol. 187, pp. 81-87.
Miller, Peter, et al., "Automated Detection of Mammographic Asymmetry Using Anatomical Features," International Journal of Pattern Recognition and Artificial Intelligence, Dec. 1993, vol. 07, No. 6, pp. 1461-1476.
Zhang, Ming, et al., "Automated detection of spiculated lesions and architectural distortions of digitized radiograms," SPIE, 1995, vol. 2434, pp. 846-854.
Wei, Datong, et al., "Classification of mass and normal breast tissue on digital mammograms: Multiresolution texture analysis", Medical Physics vol. 22, No. 09, Sep. 1995, pp. 1501-1513.
Yin, Fang-Fang, et al., "Comparison of Bilateral-Subtraction and Single-Image Processing Techniques in the Computerized Detection of Mammographic Masses", Original Investigations, Investigative Radiology vol. 28, No. 06, pp. 473-481.
Kegelmeyer, W., et al., "Computer-aided Mammographic Screening for Spriculated Lesions", Radiology, May 1994, vol. 191, pp. 331-337.
Tahoces, Pablo, et al., "Computer-assisted diagnosis: the classification of mammographic breast parenchymal patterns," Phys. Med. Biol. vol. 40, No. 01, Jan. 1995, pp. 103-117.
Yoshimura et al., "Computerized Scheme for the Detection of Pulmonary Nodules: A Nonlinear Filtering Technique", Invest. Radiol. vol. 27, No. 02, Feb. 1992, pp. 124-129.
Miller, Peter, et al., "Detection of breast asymmetry using anatomical features", SPIE, Proceedings of Biomedical Image Processing and Biomedical Visualization, vol. 1905, Jul. 29, 1993, pp. 433-442.
Sprecht, Donald, "Enhancements to Probabilistic Neural Networks", Proceedings of the IEEE International Joint Conference on Neural Networks, Baltimore, MD. Jun. 7-11, 1992, pp. I-761-I-768.
Sprecht, Donald, et al., "Experience with Adaptive Probabilistic Neural networks and Adaptive General Regression Neural Networks", IEEE International Conference on Neural Networks, Orlando, Florida. Jun. 28 to Jul. 2, 1994, pp. 1203-1208.
Katsuragawa, Shigehiko, et al., "Image feature analysis and computer-aided diagnosis in digital radiography: Effect of digital parameters on the accuracy of computerized analysis of interstitial disease in digital chest radiographs," Medical Physics, vol. 17, No. 1, 1990, pp. 72-78.
Frankel, Steven, et al., "Initial Versus Subsequent Screening Mammography: Comparison of Findings and Their Prognostic Significance", AJR, vol. 164, No. 05, May 1995, pp. 1107-1109.
Gurney, Jud, W., "Neural Networks at the Crossroads: Caution Ahead", Devil's Advocate, Radiology vol. 193, No. 01, Oct. 1994, pp. 27-28.
Doi, Kunio, et al., "Potential Usefulness of Digital Imaging in Clinical Diagnostic Radiology: Computer Aided Diagnosis", Journal of Digital Imaging vol. 8, No. 1, Feb. 1995, pp. 02-07.
Floyd, Carey, et al., "Prediction of Breast Cancer Malignancy Using an Artificial Neural Network", Cancer, vol. 74, No. 11, Dec. 1994, pp. 2944-2948.
Specht, Donald, F., "Probabilistic Neural Networks", Original Contribution, Neural Networks, vol. 3, 1990, pp. 109-118.
Ikeda, Debra, "Second-screening Mammography: One versus Two Views per Breast", Mammography, Radiology vol. 168, Issue 03, Sep. 1988, pp. 651-656.
Thurfjell, E., et al., "Sensitivity and Specificity of Computer-Assisted Breast Cancer Detection in Mammongraphy Screening," Acta Radiologica., vol. 39, 1988, pp. 384-388.
Nishikawa, Robert M., et al., "Computer-aided detection and diagnosis of masses and clustered microcalcifications from digital mammograms", Proceedings of Biomedical Image Processing and Biomedical Visualization, vol. 1905, Jul. 29, 1993, 3 pages.
Doi, Kunio, et al., "Computer aided diagnosis of breast cancer on mammograms", Breast Cancer, Springer Link, vol. 4, Issue 4, Dec. 1997, pp. 228-233.
Kegelmeyer, W. Philip, "Computer detection of stellate lesions in mammograms", Proceedings of Biomedical Image Processing and Three-Dimensional Microscopy, vol. 1660, Jun. 26, 1992, 1 page. Available at:-https://www.spiedigitallibrary.org/conference-proceedings-of-spie/1660/0000/Computer-detection-of-stellate-lesions-in-mammograms/10.1117/12.59574.short.
Yin, Fang-Fang, et al., "Computerized detection of masses in digital mammograms: Analysis of bilateral subtraction images", Medical Physics, vol. 18, Issue 5, Sep. 1991, 3 pages. Available at:-http://onlinelibrary.wiley.com/doi/10.1118/1.596610/full.
Karssemeijer, N., et al., "Detection of stellate distortions in mammograms", Browse Journals & Magazines, IEEE Transactions on

(56) References Cited

OTHER PUBLICATIONS

Medical, vol. 15, Issue 5, Oct. 1996, 3 pages (Abstract Only). Available at:-http://ieeexplore.ieee.org/abstract/document/538938/?reload=true.

Matsubara, Tomoko, et al., "Development of a New Algorithm for Detection of Mammographic Masses", SpringerLink, Digital Mammography, vol. 13, 1998, 6 pages. Available at:-https://link.springer.com/chapter/10.1007%2F978-94-011-5318-8_22.

Sa, Feig, et al., "Digital mammography, computer-aided diagnosis, and telemammography", Radiologic Clinics of North America, vol. 33, No. 06, Nov. 1, 1995, 1 page. Available at:-http://europepmc.org/abstract/med/7480666.

\* cited by examiner

FRONT VIEW INTO CABINET
Door Open

Typical Example of an X-ray Cabinet System

View in Sample Chamber with Door Open with
X-ray source at position (14) Top Center Lateral View of X-Ray Source
Mounted to Swing Arm at position (14)

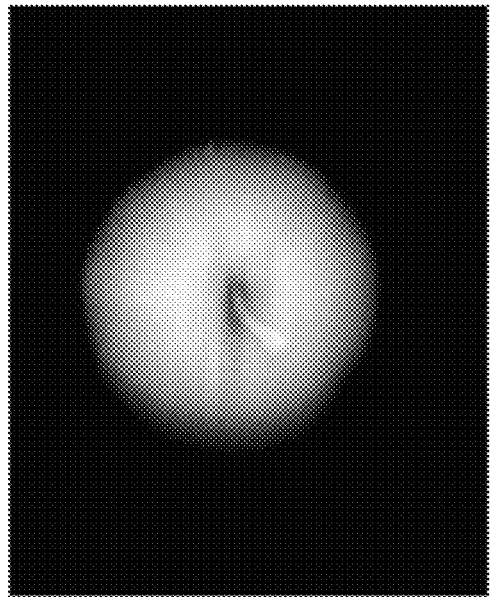
Fig. 7A - Top Slice – 59m
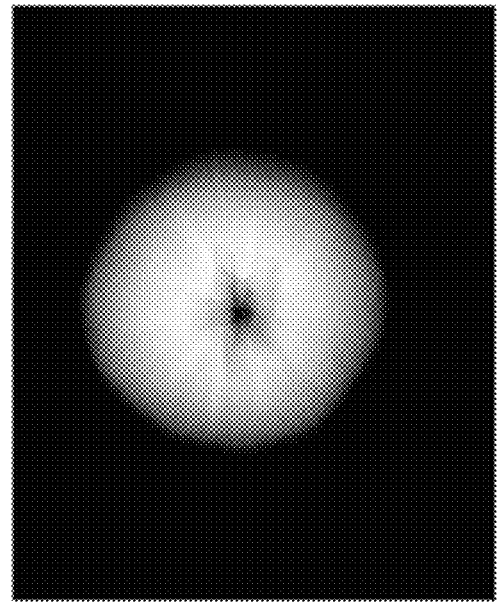
Fig. 7B - Bottom Slice – 13.5 mm
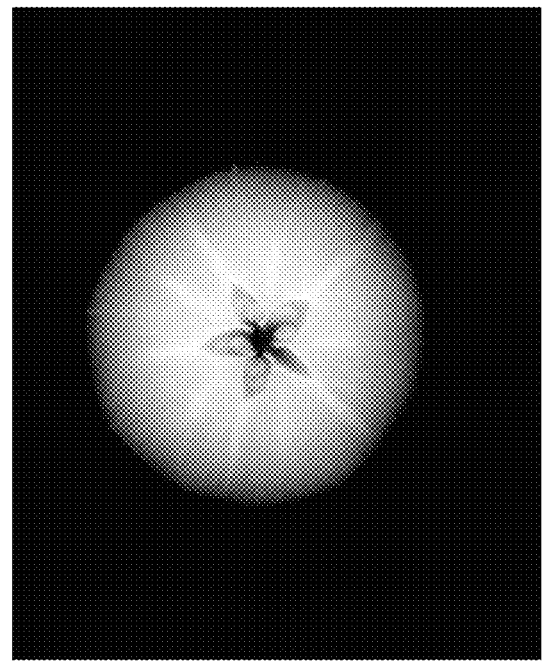
Fig. 7C - Middle Slice – 30.5 mm
Images of an Apple at multiple depth cuts
after tomosynthesis reconstruction from bottom up with the bottom at 0mm FRONT VIEW INTO CABINET
WITH GEOMETRIC MAG TRAY
Door Open Basic Rotation with Sample on Tray
to affect Geometric Magnification

SYSTEM AND METHOD FOR COMPUTER AIDED DETECTION (CAD) IN A BREAST SPECIMEN RADIOGRAPH

CROSS-REFERENCE TO RELATED APPLICATIONS

This application claims priority to and the benefit of U.S. Provisional Patent Application Ser. No. 62/396,874 filed Sep. 20, 2016, the disclosure of which is incorporated herein by reference in its entirety.

BACKGROUND

Field of the Present Disclosure

The aspects of the disclosed embodiments generally relate to computer aided diagnosis of medical images. In particular, the aspects of the disclosed embodiments generally relate to a method and apparatus for computer-aided lesion detection and calcifications using information from multiple digital breast specimen images both 2-D and tomosynthesis images for allowing more sensitive and reliable identification of suspicious, i.e., possibly cancerous, lesions and calcifications.

Background

Systems for computer-aided diagnosis ("CAD") assist radiologists in the detection and classification of abnormal lesions in medical images. The purpose of such devices, as referred to in U.S. Pat. No. 5,815,591 Roehrig, et. al., entitled "Method and Apparatus for Fast Detection of Spiculated Lesions in Digital Radiograms," the disclosure of which is hereby incorporated by reference in the present application, is to direct the attention of a radiologist to suspicious areas of the medical image that may reflect a threatening condition. While not a replacement for the experienced radiologist, CAD systems are designed to increase efficiency and reduce error, as a typical radiologist may be required to examine hundreds of medical images per day, which can lead to the possibility of a missed diagnosis due to human error.

Currently it is believed that there is not a system or method for the utilization of CAD in Digital Breast Specimen Radiography/Tomosynthesis.

Desired characteristics of a CAD system for analyzing Digital Breast Specimen Radiographs (DBSR) include higher sensitivity, i.e., the ability to detect more subtle indications of abnormalities, coupled with lower false positive rates, i.e., the number of areas marked "suspicious" by the CAD system which, in reality, are not suspicious or indicative of a possibly cancerous condition. Generally speaking, it is desirable to minimize both the rate of false negatives, also called "misses", as well as the rate of false positives.

Today, conventional breast specimen systems usually treat each digital breast specimen radiogram separately. In these systems, the plurality of radiograms that are usually taken of a woman's breast specimen are viewed separately for detecting suspicious lesions. Suspicious lesions are located on each of the images separately, without regard for what regions are found or not found in the other images.

However, in radiology practice it has been found that if the same abnormality appears in two different views of the same specimen, then that abnormality has a higher probability of being a true lesion, such as a cancerous lesion in, for example, breast tissue. This is because normal overlying tissue structures may erroneously appear to be an abnormal lesion in a single digital breast specimen radiograph, but the same tissue structures which will appear different or void of a lesion in a different view. Accordingly, there is a lower probability of false positives when two different views of the same tissue specimen are examined, due to the lower probability of false or accidental crossing of tissue structure indicating a lesion in the same region on two separate views of, for example, one breast specimen.

In comparing multiple views of a single breast specimen, it is necessary to have a common reference from which to measure the location of potentially suspicious lesions in each view. One such reference point can be the nipple of the breast, if included in the view. A problem arises, however, in that the breast is often manipulated during the specimen radiography process in various ways, such that the nipple may be in different and sometimes unpredictable locations in the digital radiogram. The nipple may, or may not, correspond to the location along the skin line furthest from the specimen base.

The use of CAD being utilized in DBSR, the use of CAD in DBSR shall be referred to as Digital Breast Tomosynthesis (DBT).

In "Computerized detection of masses in digital radiograms: Analysis of bilateral subtraction images," Med. Phys. 18 (5), September/October 1991, Yin and Giger et. al. refer to a bi-lateral subtraction technique, in which one image is rotated and translated to best match the other image, and then left and right images are subtracted from each other pixel-by-pixel. The resulting difference image is then thresholded to obtain several "starting points" which represent the areas of largest difference between left and right breasts. However, in the Yin and Giger et. al. disclosure, it is only raw pixels that are compared between left and right breasts, and the simple output obtained is only a starting point for further analysis.

In U.S. Pat. No. 5,579,360, Abdel-Mottaleb refers to mass detection by computer using digital radiograms of the same breast taken from different viewing directions. Abdel-Mottaleb refers to a method in which position, size, shape, intensity variance, and brightness are each directly compared between the two views of the same breast. The Abdel-Mottaleb method is disadvantageous, however, in that if any one such measure between views does not correlate within specified boundaries, the suspect spot is marked as a false positive, whereas correlated spots meeting all criteria lead directly to a mark on the output display directing the attention of the radiologist to that spot. Such a binary approach can often accord inordinate weight to the inter-view comparison process, at the expense of strong indicators that may still exist within a single view.

It would be desirable to provide a computer-aided diagnosis system that uses information from multiple digital specimen radiographs to provide sensitive, fast, and reliable identification of suspicious, lesions in a DBSR-digital breast specimen radiograph.

It would be further desirable to provide a computer-aided diagnosis system that processes information from a first digital view of a breast specimen, together with comparative information from a plurality of views of the same breast specimen, to arrive at an overall suspiciousness determination regarding potentially suspicious lesions in the first digital breast specimen view.

It would be still further desirable to provide a computer-aided diagnosis system that processes information from a first digital breast specimen radiogram view of a breast, together with comparative information from a different digital breast specimen radiogram view of the same breast specimen, to arrive at an overall suspiciousness determination regarding potentially suspicious lesions in the first digital specimen radiograph view.

DESCRIPTION OF THE RELATED ART

In the field of x-ray mammography, thousands of x-ray mammography CAD systems and digital breast specimen systems are now installed worldwide, and are used to assist radiologists in the interpretation of millions of radiograms and breast specimen images per year. X-ray mammography CAD systems are described, for example, in U.S. Pat. Nos. 5,452,367, 5,572,565, 5,729,620, 5,815,591, 5,917,929, 6,075,879, 6,266,435, 6,301,378, 6,434,262, and 6,901,156, each of which is incorporated by reference herein. X-ray mammography CAD algorithms analyze digital or digitized images of standard mammographic views (e.g. CC (cranial caudal), MLO (mediolateral-oblique)) for characteristics commonly associated with breast cancer, such as calcifications, masses, and architectural distortions. CAD systems for use with other modalities such as breast MRI, breast CT, and breast ultrasound imaging are also in various stages of development, although none yet approaches x-ray mammography in terms of widespread acceptance and adoption.

It would be desirable to provide a CAD system for use in breast specimen cancer screening that provides even better performance in the identification of imaged tissue features that may be indicative of a cancerous condition. It would be further desirable to provide a CAD user interface accommodating such improved functionality.

Specimen Radiography is considered the most cost-effective screening method for the detection of breast cancer in surgically removed breast tissue. However, the sensitivity of specimen radiography is often limited by the presence of overlapping dense fibroglandular tissue in the breast specimen. Dense parenchyma reduces the conspicuity of abnormalities and thus constitutes one of the main causes of missed breast cancer diagnosis. The advent of full-field digital detectors offers opportunities to develop advanced techniques for improved imaging of dense breasts, such as digital tomosynthesis.

Digital tomosynthesis is based on the same principle as conventional tomography, which involves the use of a screen-film-detector system as the image receptor for imaging body parts at selected depths. With conventional tomography, a series of projection exposures is accumulated on the same film when the x-ray source is moved about a fulcrum while the screen-film system is moved in the opposite direction. A drawback of conventional tomography is that each tomogram can depict only one plane at a selected depth with a relatively sharp focus. If the exact depth of interest is not known in advance or the abnormality encompasses a range of depths, then a tomogram at each depth will have to be acquired at separate imaging examinations, requiring additional radiation doses and examination time.

With digital tomosynthesis, the series of projection exposures is read out by the digital detector as separate projection views when the x-ray source moves to different locations about the fulcrum. Tomographic sections focused at any depth of the imaged volume can then be generated from the same series of projection images by using digital reconstruction techniques. Because of the wide dynamic range and the linear response of the digital detector, each projection image can be acquired with a fraction of the x-ray exposure used to obtain a conventional projection radiograph. The total radiation dose required for digital tomosynthesis imaging may be kept at nearly the same as or only slightly higher than that required for conventional radiography. Properly designed digital reconstruction techniques have an additional advantage in that the depth resolution of tomosynthesis is generally much higher than that of conventional tomography. Thus, digital tomosynthesis makes it more practical to apply tomography to breast imaging in terms of radiation dose, examination time, and spatial resolution.

Digital breast specimen tomosynthesis the systems and methods included in U.S. Pat. No. 2015/0131773 (U.S. Pat. No. 9,138,193), Lowe, et. al., entitled "SPECIMEN RADIOGRAPHY WITH TOMOSYNTHESIS IN A CABINET," the disclosure of which is hereby incorporated by reference in its entirety in the present application, with the incorporation of aspects of the disclosed embodiments included herein is a promising method that may help reduce the camouflaging effects of dense breast tissue and improve the sensitivity of specimen radiography for breast cancer detection in dense breasts.

Computer-aided detection (CAD) has been shown to improve breast cancer detection at mammography. Although the results of a preliminary evaluation indicated that breast lesions can be visualized more easily on Digital Breast Specimen Tomosynthesis (DBST) images than on conventional digital breast specimen radiograms. With DBST, the number of reconstructed sections of each breast specimen is very large. Even with 1-mm section thickness, the number of sections per breast specimen may range from about 30 to more than 60. The time required to interpret a DBST case can be expected to be much longer than that required to interpret a conventional mammographic case. With increases in radiologist workloads, the possibility of subtle lesions being overlooked may not be negligible. CAD will probably have a role in the reading of DBST radiograms. Thus, the purpose of aspects of the disclosed embodiment is a CAD system for the detection of masses in DBST specimen radiography and to perform a preliminary evaluation of the performance of this system.

Breast cancer is the most common cancer among women other than skin cancer, and is the second leading cause of cancer death in women after lung cancer. The American Cancer Society currently estimates that there are about 182,460 new cases of invasive breast cancer per year among women in the United States and 40,480 deaths per year from the disease. Prevention and early diagnosis of breast cancer are of foremost importance. Because early breast cancer does not produce symptoms, the American Cancer Society recommends an x-ray radiogram screening and a clinical breast examination every year for women over the age of 40. Recently, the American Cancer Society has additionally recommended an adjunctive breast MRI (magnetic resonance imaging) screening for women in certain higher-risk groups. Although aspects of the embodiments described herein below, particularly aspects of the preferred embodiments, are particularly applicable and advantageous for use in x-ray mammography and x-ray tomosynthesis breast cancer screening environments, they are also readily applicable for other breast imaging modalities such as breast specimen radiography and digital breast specimen tomosynthesis.

Computer-aided detection (CAD) generally refers to the use of computers to analyze medical images to detect anatomical abnormalities in the subject body part. Sometimes used interchangeably with the term computer-aided detection are the terms computer-aided diagnosis, computer-assisted diagnosis, or computer-assisted detection. Upon acquisition of a digital or digitized medical image, a CAD algorithm processes the medical image to detect locations thereon having sufficient likelihood of being associated with an abnormal condition to qualify as a CAD detection, i.e., to qualify as a location on the image that warrants particular attention by a radiologist (or other suitable medical professional) for closer analysis. The CAD algorithm usually identifies a preliminary set of candidate locations in a medical image and then selects which ones, if any, will qualify as actual CAD detections based on a variety of computed features associated with the candidate detections. The CAD results are most often communicated in the form of annotation maps comprising graphical annotations (CAD markers) overlaid on a diagnostic-quality or reduced-resolution version of the medical image, one CAD marker for each CAD detection.

AD results can be used by radiologists as "secondary reads" or secondary diagnosis tools. When analyzing a medical image, the radiologist usually makes his or her own analytical determinations before looking at the CAD results, which either verify those determinations or trigger further inspection of the image. Some CAD implementations have used CAD results in a "concurrent reading" context in which the radiologists look at the CAD results at the same time that they look at the actual images, for example, tomosynthetic images.

SUMMARY

A system, method, and computer program product are provided for computer-aided detection of suspicious lesions in digital breast specimen radiograms, wherein single-view feature vectors from a first digital breast specimen radiogram are processed in a classification algorithm along with information computed from a plurality of related digital breast specimen radiograms to assign an overall probability of suspiciousness to potentially suspicious lesions in the first digital breast specimen radiogram. In a preferred embodiment, a first digital breast specimen radiogram and a second digital breast specimen radiogram taken from a different view of the same are processed, with single-view feature vectors corresponding to potentially suspicious lesions being separately computed for each digital breast specimen radiogram and then compared to produce similarity metrics. If a potentially suspicious lesion in the first digital breast specimen radiogram has a high degree of similarity with a potentially suspicious lesion in the second digital breast specimen radiogram, there is a greater probability that the potentially suspicious lesion is a true lesion.

In another preferred embodiment, a first digital breast specimen radiogram and multiple other breast specimen radiograms taken and/or computed via tomosynthesis are processed, with single-view feature vectors of potentially suspicious lesions being separately computed for each digital breast specimen radiogram and then compared to produce symmetry metrics to verify if the suspicious lesions are truly lesions of concern.

In still another embodiment, a method for detecting suspicious lesions in a breast using information from a first digital breast specimen radiogram view of the breast and a second digital breast specimen radiogram view of the breast using a cabinet x-ray system. The cabinet x-ray system includes a cabinet defining an interior chamber; an x-ray source, an x-ray detector, a specimen platform, and a motion control mechanism configured for moving the x-ray source to or along a plurality of positions within the interior chamber relative to the specimen disposed on the specimen platform; and a controller configured to selectively energize the x-ray source to emit x-rays through the specimen to the x-ray detector at selected positions of the x-ray source relative to the specimen. The method includes controlling the x-ray detector to collect projection x-ray images of the specimen when the x-ray source is energized at the selected positions such that the isocenter of the emitted x-rays at the selected positions is located at a surface of the x-ray detector, wherein one of the projection x-ray images is a two-dimensional x-ray image taken at standard imaging angle of approximately 0°; creating a tomosynthetic x-ray image reconstructed from a collection of projection x-ray images; processing the collection of the projection x-ray images in the controller into one or more reconstructed tomosynthetic x-ray images representing a volume of the specimen and relating to one or more image planes that are selectively the same or different from that of the two-dimensional x-ray image; locating a first set of potentially suspicious lesions in said first digital breast specimen radiogram view from a first reconstructed tomosynthetic x-ray image, each of said first set of potentially suspicious lesions having, each of said first set of potentially suspicious lesions having a first single-view feature vector corresponding thereto corresponding thereto; locating a second set of potentially suspicious lesions in said second digital breast specimen radiogram view from a second reconstructed tomosynthetic x-ray image, each of said second set of potentially suspicious lesions having a second single-view feature vector corresponding thereto; computing a similarity metric between each of said first set of potentially suspicious lesions and each of said second set of potentially suspicious lesions using the first single-view feature vector corresponding to said first set of potentially suspicious lesions and the second single-view feature vector corresponding to said second set of potentially suspicious lesions; and classifying each of said first set of potentially suspicious lesions using information from the corresponding single-view feature vector and from the corresponding similarity metrics.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and that, unless otherwise indicated, they are merely intended to conceptually illustrate the structures and procedures described herein. In addition, any suitable size, shape or type of elements or materials could be used.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 7A, 7B and 7C—Displays the results of the imaging of an apple at multiple depth cuts after tomosynthesis reconstruction in a cabinet X-ray system incorporating aspects of the present disclosure.

DETAILED DESCRIPTION

The systems and methods of the present disclosure address the needs of the art by providing tomosynthesis apparatus and techniques for imaging breast specimens that overcome the shortfall of the data received from two-dimensional imaging systems. The aspects of the present disclosure enable the use of tomosynthesis to efficiently provide accurate three-dimensional imaging of a specimen in which overlapping images having differing attenuation characteristics by applying a three-dimensional reconstruction algorithm all in an x-ray cabinet with the option of providing geometric magnification of the specimen.

As used herein, the term "computer," "computer system" or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine readable instructions, program or library of routines capable of executing on a computer or computer system including computer readable program code.

Aspects of the disclosed embodiments relate to the adaption of the CAD utilization in mammography for utilization in Digital Breast Specimen Imaging. Although "Digital Breast Specimen Tomosynthesis" can be used to obtain a series of related films or views, it can also be used to depict one such view of an object as well. As used herein, the term "Specimen Radiogram" shall correspond to a one of the related films or views taken during the Digital Breast Specimen radiography process in which a series of films or views is obtained or only one film or view is obtained.

Figure 1:
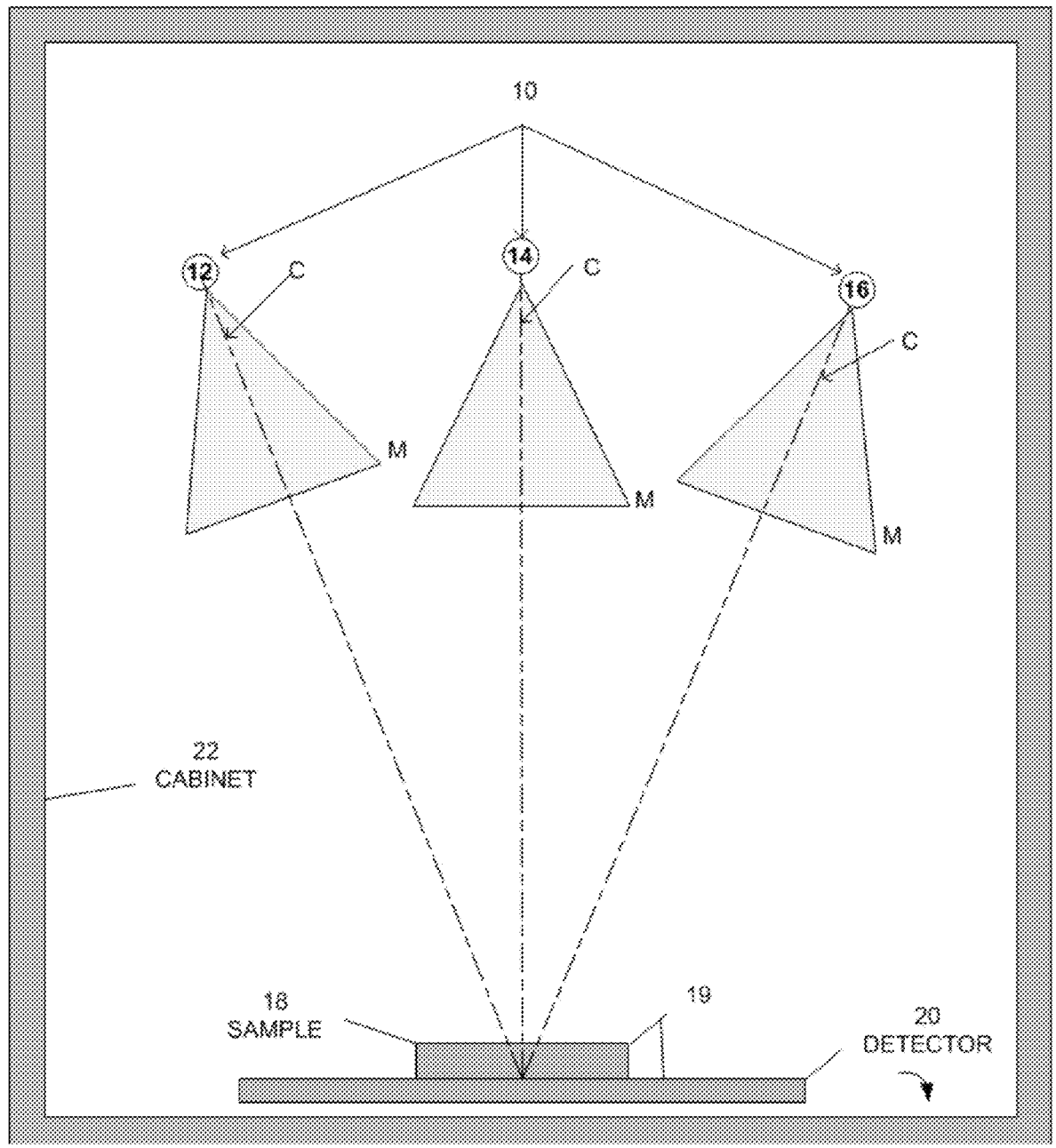
FIG. 1—Schematically illustrates a front view of an X-ray source, a specimen/sample, and a digital detector, where the X-ray source moves relative to the specimen for imaging the specimen at different angles, in one embodiment of a system incorporating aspects of the present disclosure.

Specimen Tomography is a three-dimensional specimen imaging system. It involves acquiring images of a sample at multiple viewpoints, typically over an arc or linear path. The three-dimensional image is constructed by the reconstruction of the multiple image data set. One embodiment of a system incorporating aspects of the present disclosure is illustrated in FIG. 1. The system is totally enclosed or housed in an X-ray cabinet 22. The aspects of the present disclosure include arc or linear travel of the x-ray source (10) over about a 20° to about a 50° arc, preferably about 30°, more preferably about 20°. The movement can be clockwise or counter clockwise along a path, which includes for example, one or more, or a combination thereof, of the following exemplary ranges: between approximately 350° (reference 12) to 0° (reference 14) to 10° (reference 16) or between approximately 340° (reference 12) to 0° (reference 14) to 20° (reference 16) or between approximately 335° (reference 12) to 0° (reference 14) to 25° (reference 16). The ranges recited herein are intended to be approximate and inclusive of start and endpoints. The detector 20 is stationary as is the sample 18 and is an x-ray detector and can include, for example, a flat panel x-ray detector, a flat panel digital x-ray detector. The reference "C" at each of the positions 12, 14, 16 of the X-ray source 10 in FIG. 1 refers to the point source of the X-ray beam. The reference "M" refers to the spread or fan of the X-ray beam.

In operation, source 10 is energized to emit an x-ray beam throughout its travel. The x-ray beam travels through the sample 18 to the detector 16 and the multiple images collected at varying angles are stored and then utilized for the tomosynthesis reconstruction. With the sample 18, also referred to as the "object" or "imaging object", sitting on the detector 16 a 1:1 geometric magnification image is attained.

Different embodiments can utilize different ranges of motion of one or more of the source 10 and detector 20 as well as changing the angularity of one or both. The inventive aspects of the present disclosure differ from prior systems in that either both the detector and source move and/or the isocenter is above the sample and not at the detector surface. In accordance with the aspects of the present disclosure, in one embodiment, the source 10 may be configured to move or rotate, as is described herein, while the detector 20 is configured to remain stationary or in a fixed position.

Detector 20 and associated electronics generate image data in digital form for each pixel at each of the angular positions of source 10 and translations positions of the detector 20 relative to the sample 18. While only three positions are illustrated in FIG. 1, in practice more images are taken at differing angles, i.e. approximately every 1° of rotation or motion of source 10.

In operation, X-ray source 10 is energized to emit an X-ray beam, generally throughout its travel along one or more of the paths or positions described above. The X-ray beam travels through the sample 18 to the detector 20 and the multiple images collected at varying angles are stored and then utilized for the tomosynthesis reconstruction. The X-ray source 10 may range from about 0 kVp to about 90 kVp, preferably a 50 kVp 1000 µa X-ray source.

Different embodiments of the present disclosure can utilize different ranges of motion of one or more of the X-ray source 10 and detector 20 as well as changing the angularity of one or both. The inventive aspects of the present disclosure differ from the prior art in that in prior art systems either the detector and X-ray source 10 and/or the isocenter is above the sample and not at the detector surface. In accordance with the aspects of the present disclosure, in one embodiment, the X-ray source 10 is configured to move, as is described herein, while the detector 20 is configured to remain stationary or in a fixed position.

The detector 20 and associated electronics generate image data in digital form for each pixel at each of the angular positions 12, 14, 16 of X-ray source 10 and translation positions of the detector 20 relative to the sample 18. While only three positions 12, 14, 16 are illustrated in FIG. 1, in practice more images are taken at differing angles. For example, in one embodiment, images can be taken at approximately every 1° of rotation or motion of source 10.

Figure 2:
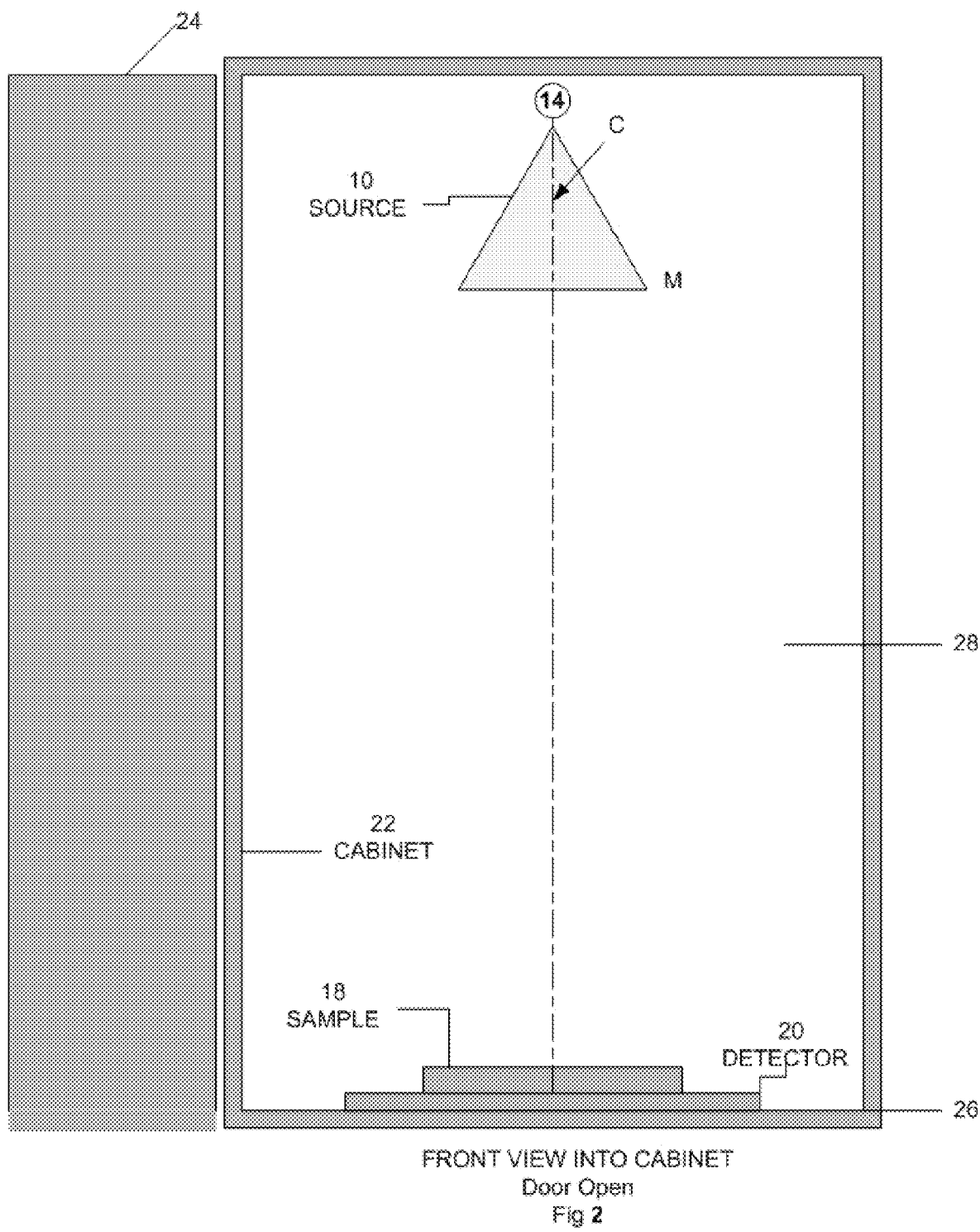
FIG. 2—Schematically illustrates an exemplary orientation of the X-ray source, specimen, and digital detector as viewed when the door of the cabinet is open, in one embodiment of a system incorporating aspects of the present disclosure.

FIG. 2 schematically illustrates one embodiment of the orientation of the X-ray source 10 as seen when the door 24 is opened and the X-ray source 10 is locate at approximately 0°, reference point 14 in this example, within the X-ray cabinet 22. In this embodiment, the motion of the X-ray source 10 can generally occur from the back to the front of the X-ray cabinet 22 with the detector 20 oriented, or otherwise disposed, at the base 26 of the X-ray cabinet 22, within the X-ray cabinet chamber 28. In one embodiment, the detector 20 is suitably coupled to the base 26 of the X-ray cabinet 22. The X-ray spread in this example can be from about 0 kVp to about 50 kVp with the system preferably utilizing an AEC (Automatic Exposure Control) to ascertain the optimal setting to image the object or sample 18 being examined.

In one embodiment, the detector 20, X-ray source 10, and the swing arm 60 (FIG. 5) servo mechanism are controlled via a combination of one or more of software and hardware, such as non-transitory machine readable instructions stored in a memory that are executable by one or more processors. On example of such a configuration can include controller cards of a computer 470 (FIG. 4), such as a MS Windows based computer. In one embodiment, non-transitory machine readable instructions being executed by one or more processors of the computer 470 is utilized to compile data received from the detector 20 and present resulting images to a suitable display or monitor 472 (FIG. 4) at each imaging position, such as positions 12, 14 and 16 shown in FIG. 1, the detector 20 generates the respective digital values for the pixels in a two-dimensional array. The size of detector 20 may range, for example, from about 5.08 centimeters by 5.08 centimeters to about 40.64 centimeters by 40.64 centimeters, preferably about 12.7 centimeters by 15.24 centimeters. In one example, detector 20 has a rectangular array of approximately 1536×1944 pixels with a pixel size of 74.8 micrometers. The image dataset attained at each respective position may be processed either at the full spatial resolution of detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the detector 20 or within the computer 470 providing the tomosynthetic compilation and image.

Figure 3:
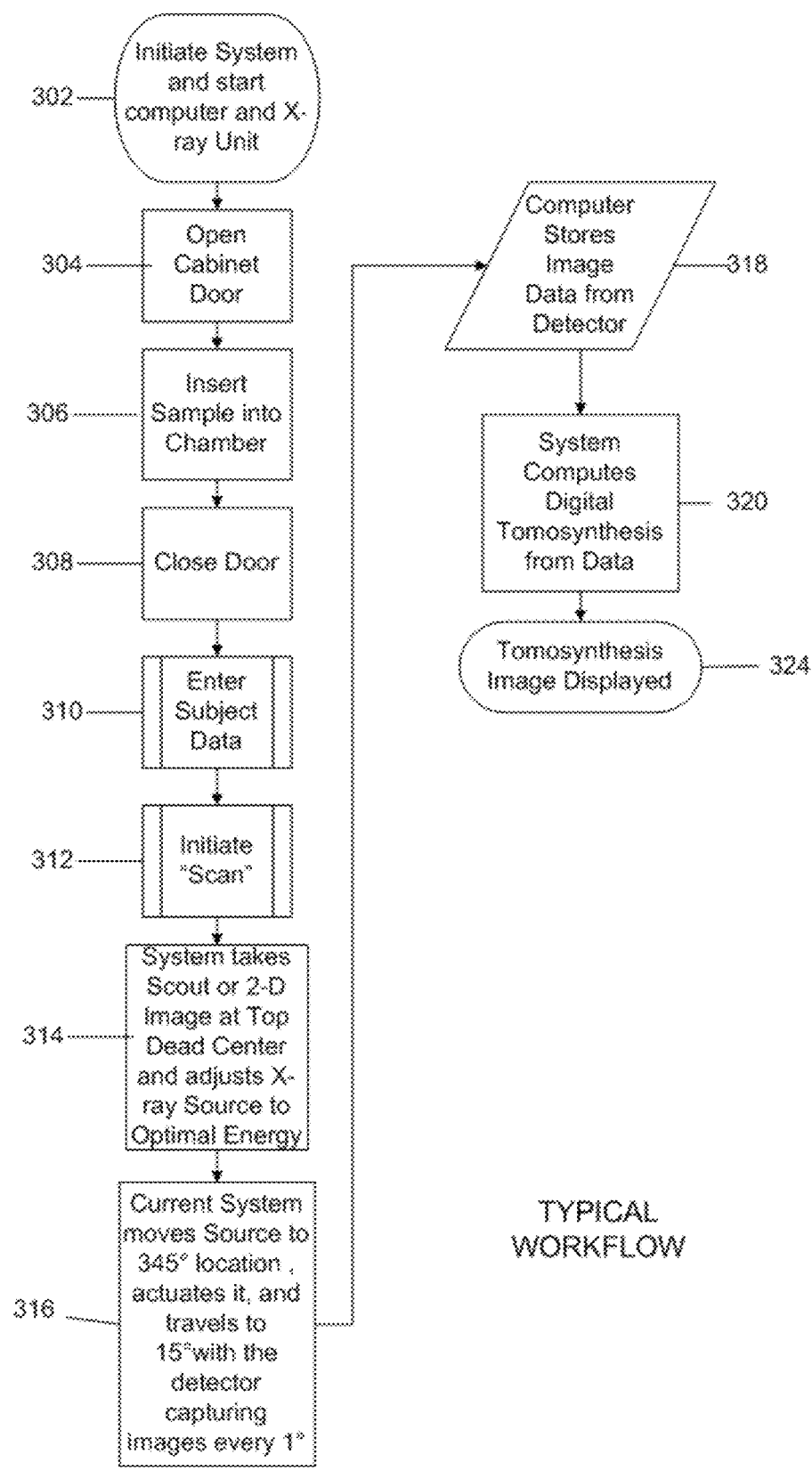
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system exemplified in FIG. 1, for example, is initiated 302, the X-ray cabinet door 24 opened 304, and the sample 18 placed into 306 the X-ray cabinet chamber 28. As shown in FIG. 2, for example, the sample 18 is positioned on the detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2. The X-ray source 10 can then be moved to other positions, such as positions 12 and 16, and the detector 20 can be used to capture 316 images at various increments along the travel path of the X-ray source 10, such as about every 1 degree. The captured images are stored 318 and digital tomosynthesis is performed 320. The tomosynthesis image is then displayed 324.

Figure 4:
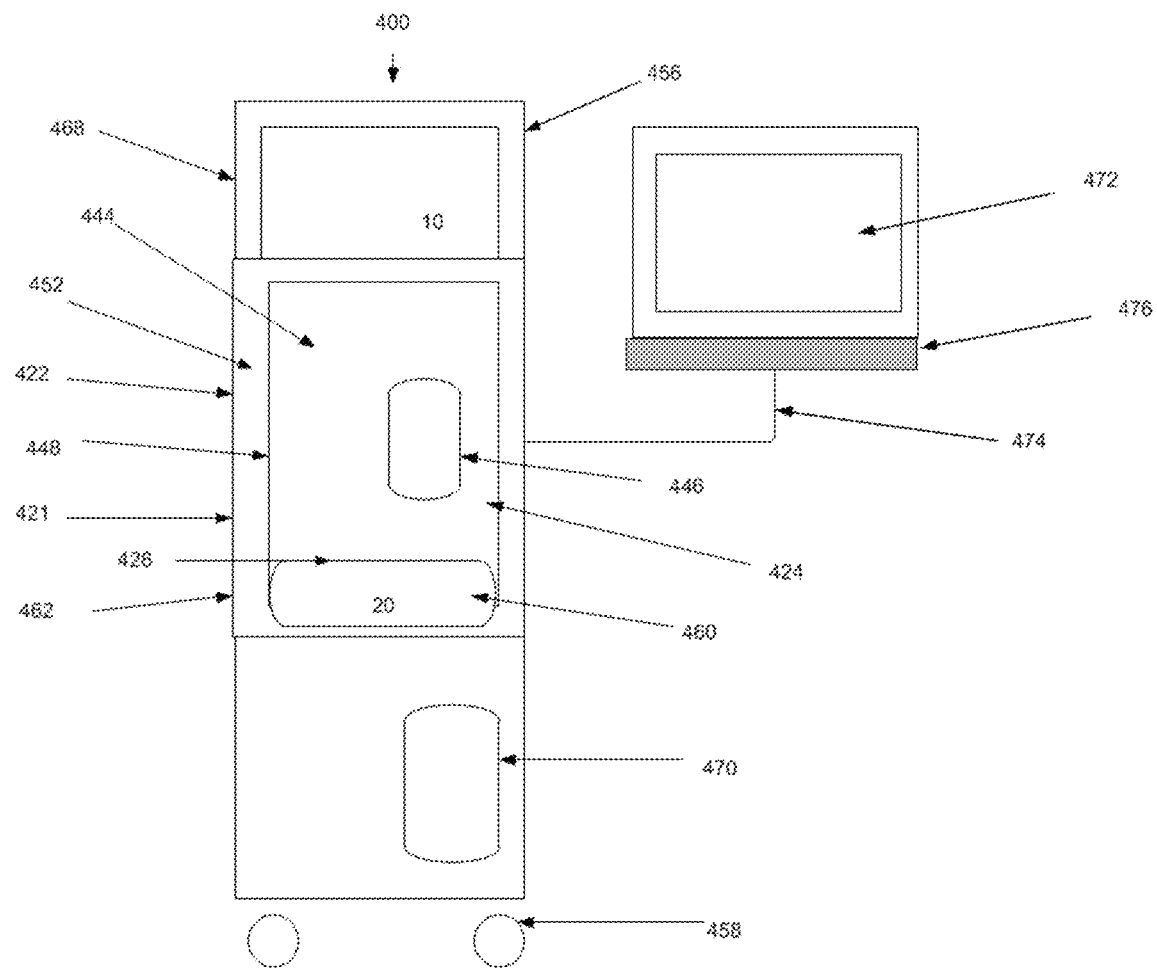
FIG. 4—Displays an example of an X-ray Cabinet System incorporating aspects of the present disclosure.

FIG. 4 shows one embodiment of an X-ray Cabinet System 400 incorporating aspects of the present disclosure. In this embodiment, the X-ray Cabinet System 400 is mounted on wheels 458 to allow easy portability. In alternate embodiments, the X-ray Cabinet System 400 can be mounted on any suitable base or transport mechanism. The cabinet 422 in this example, similar to the exemplary X-ray cabinet 22 of FIG. 1, is constructed of a suitable material such as steel. In one embodiment, the cabinet 422 comprises painted steel defining a walled enclosure with an opening or cabinet chamber 428. Within the cabinet chamber 428, behind door 424, resides an interior space forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the X-ray source 10. In the example of FIG. 4, the X-ray source 10 is located in the upper part 456 of the cabinet 422, in the source enclosure 468. The detector 20 is housed in the detector enclosure 460 at an approximate midpoint 462 of the cabinet 422.

Figure 5:
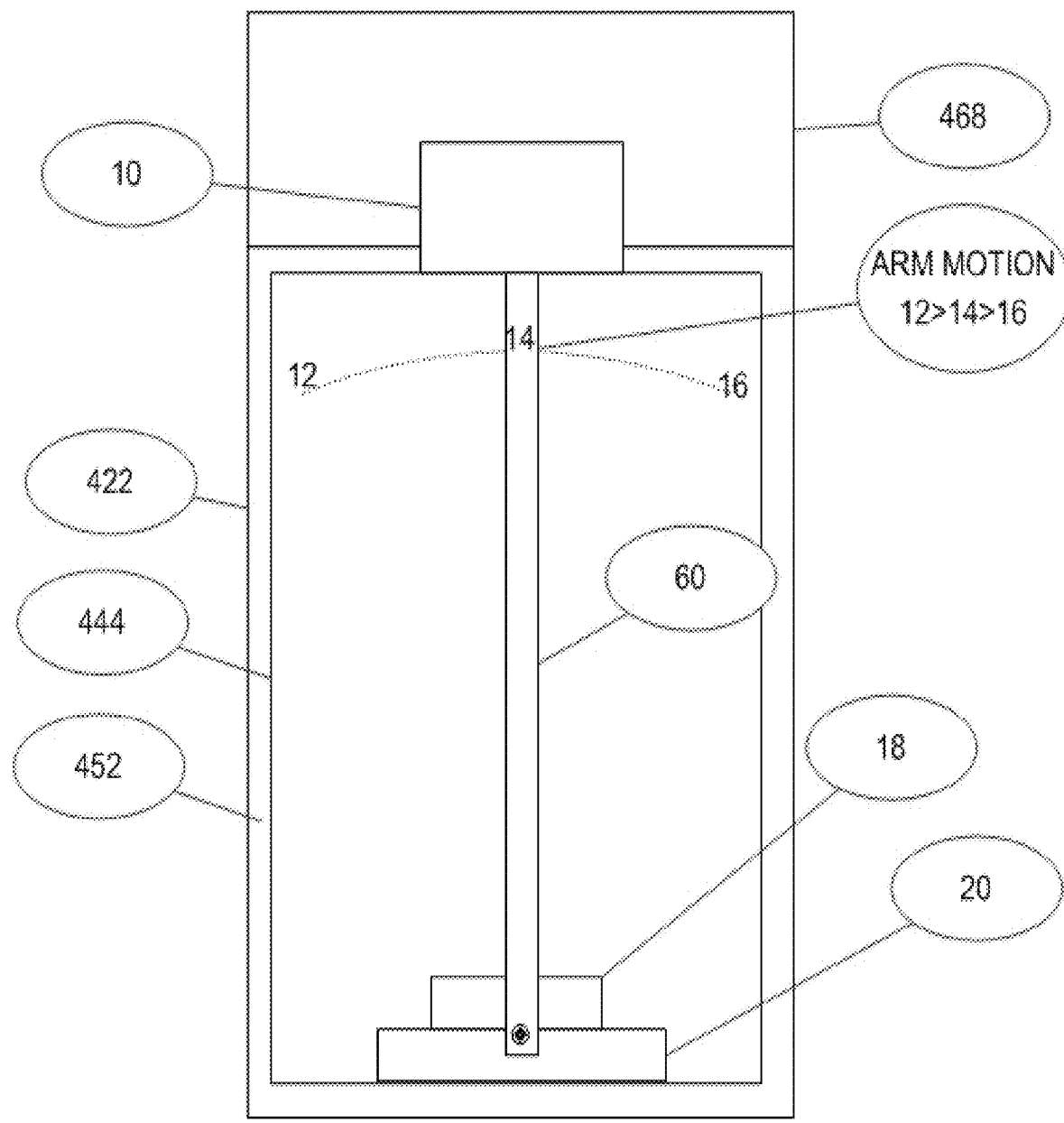
FIG. 5—Displays the sample chamber of the embodiment of FIG. 4 with the swing arm and a detector.
Figure 6:
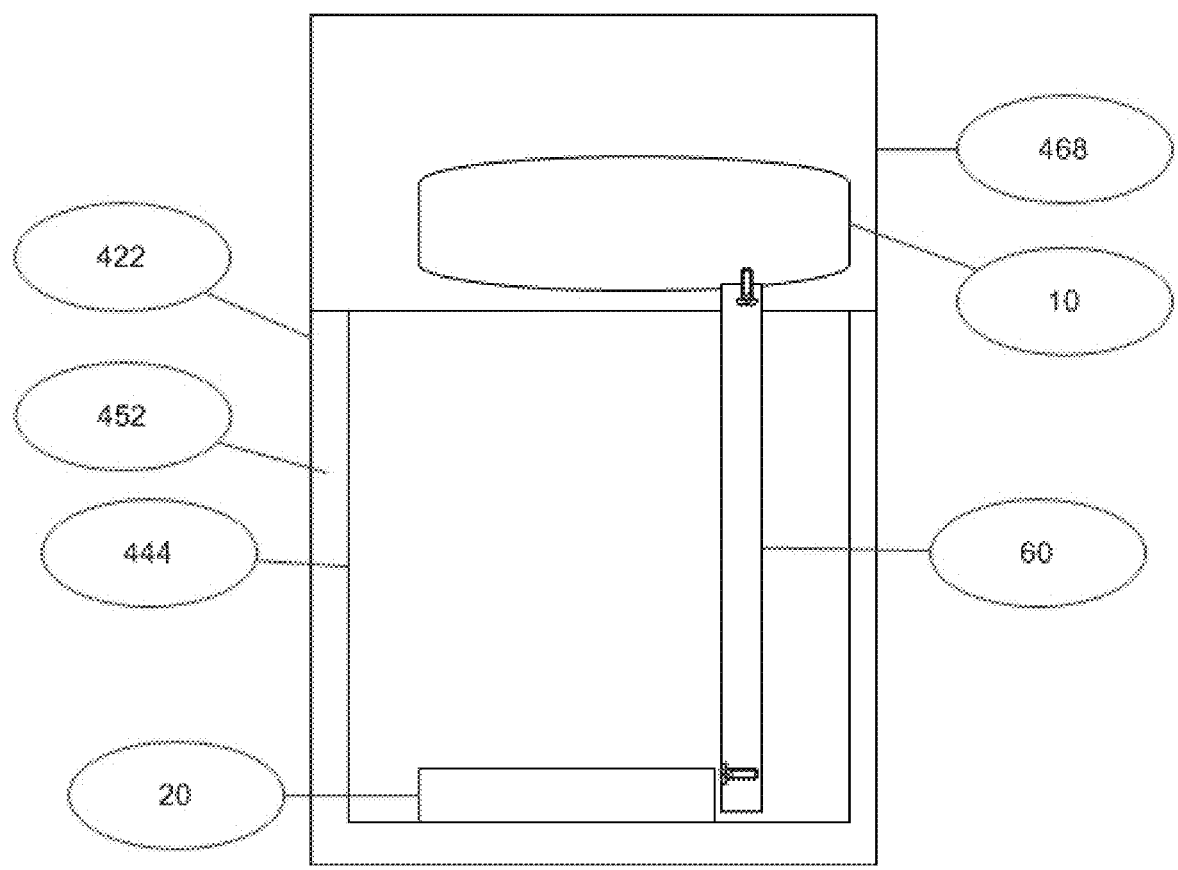
FIG. 6—Displays the lateral view of the X-ray source of the embodiment of FIG. 4 mounted to the top of the swing arm.

In one embodiment, a controller or computer 470 controls the collection of data from the detector 20, controls the swing arm 60 shown in FIGS. 5 & 6, and X-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, mini computers, tablets and pad devices.

The computer 470 can be configured to communicate with the components of the X-ray cabinet system 400 in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the X-ray source 10 and detector 20 to activate image collection while the swing arm 60 is moving along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the X-ray source 10 and the detector 20 to cease operating. The individual 2-dimensional (2-D) images which were collected, in this example at 1° increments, are then tabulated in the computer 470 to create the tomosynthetic images. In one embodiment, the operator may select which images they wish via the user interface 476 as they are being displayed on the monitor 472. In one embodiment, the devices and components of the X-ray cabinet system 400 are suitably communicatively coupled together, including one or more of hard wire connections or wireless connections using a suitable wireless connection and communication transmission protocol, as will generally be understood. The X-ray cabinet system 400 can also be configured to transfer images via USB, CD-ROM, or WIFI.

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications. FIGS. 7A, 7B, and 7C illustrate exemplary images of an apple using the above process. FIG. 7A is an image of a slice of the apple at it's very top. 59 mm from the bottom. FIG. 7B is an image of an apple computed at 30.5 mm up from the detector, and FIG. 7C is a view of the apple computed at 13.5 mm from the bottom.

The dynamic imaging software reconstructs three-dimensional images (tomosynthesis) from two-dimensional projection images in real-time and on-demand. The software offers the ability to examine any slice depth, tilt the reconstruction plane for multiplanar views and gives higher resolution magnifications (FIG. 7). Real-time image reconstruction enables immediate review, higher throughput, and more efficient interventional procedures reducing patient call backs and data storage needs. Multiplanar reconstruction enables reconstruction to any depth, magnification and plane, giving the viewer the greater ability to view and interrogate image data, thereby reducing the likelihood of missing small structures. Built-in filters allow higher in-plane resolution and image quality during magnification for greater diagnostic confidence. Software is optimized for performance using GPU technology.

The reconstruction software provides the users greater flexibility and improved visibility of the image data. It reconstructs images at any depth specified by the user rather than at fixed slice increments. With fixed slice increments, an object located between two reconstructed slices, such as a calcification, is blurred and can be potentially missed. The software can position the reconstruction plane so that any object is exactly in focus. This includes objects that are oriented at an angle to the detector; in the software the reconstruction plane can be angled with respect to the detector plane.

Figure 8:
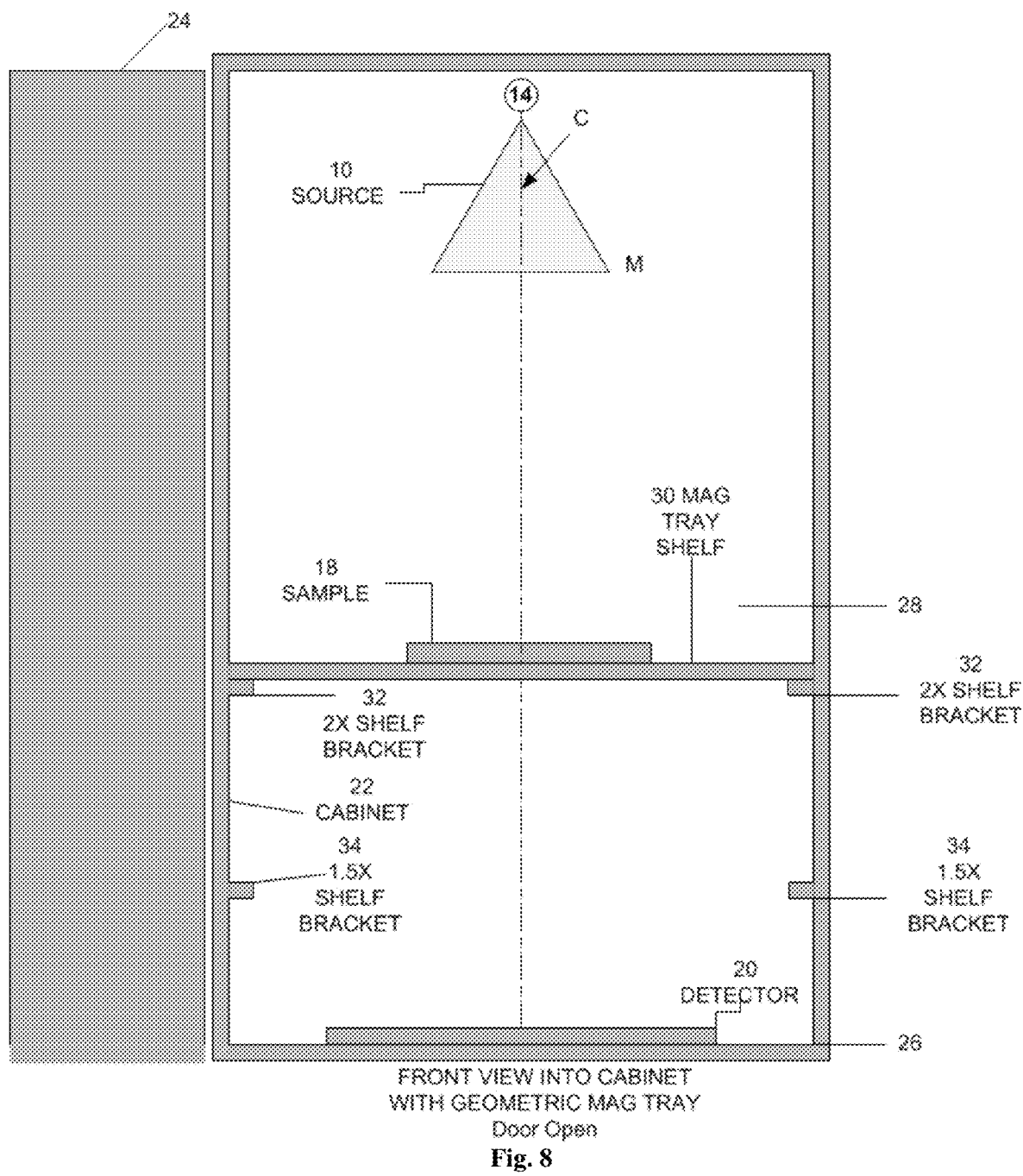
FIG. 8—Displays FIG. 2 but with the sample geometrically magnified on a raised sample tray as well as the magnification shelfs brackets in one embodiment of a system incorporating aspects of the present disclosure.

Another embodiment of a system incorporating aspects of the present disclosure is illustrated in FIG. 8. FIG. 8 schematically illustrates the orientation of the mechanism as seen when the door is opened and the mechanism is located at approximately 0° 14, similar to FIG. 2. Motion of the source 10 will generally occur from the back to the front with the detector 20 orientated at the base of the cabinet chamber 22. The reference "C" refers to the point source of the X-ray beam. The reference "M" refers to the spread or fan of the X-ray. Illustration is provided when the sample is elevated above the detector on the magnification tray 30 to affect geometric magnification. Geometric magnification is achieved by moving the movable magnification tray 30 closer to the x-ray source 10 brackets on which the magnification tray 30 is supported, the brackets being to mounted (permanently or temporarily) to the sides (interior walls) of the cabinet at different distances from the detector 20. In this example, brackets 32 could produce a 2× magnification of sample 18 when magnification tray 30 with sample 18 is positioned on brackets 32 and brackets 34 could produce a 1.5× magnification of sample 18 when magnification tray 30 with sample 18 is positioned on brackets 34. However, these are exemplified magnification powers and shelf bracket heights and are not to be considered limiting. If we affix shelf bracket 32 and the magnification tray 30 closer to the x-ray source 10 we will attain a greater geometric magnification—3× or more. The magnification tray 30 is normally kept outside the x-ray chamber 28, for example, when sample 18 is positioned on detector 20, as illustrated, for example, in FIG. 1. and is constructed of a radio translucent (x-ray transparent) material such as plastic or carbon fibre.

Figure 9:
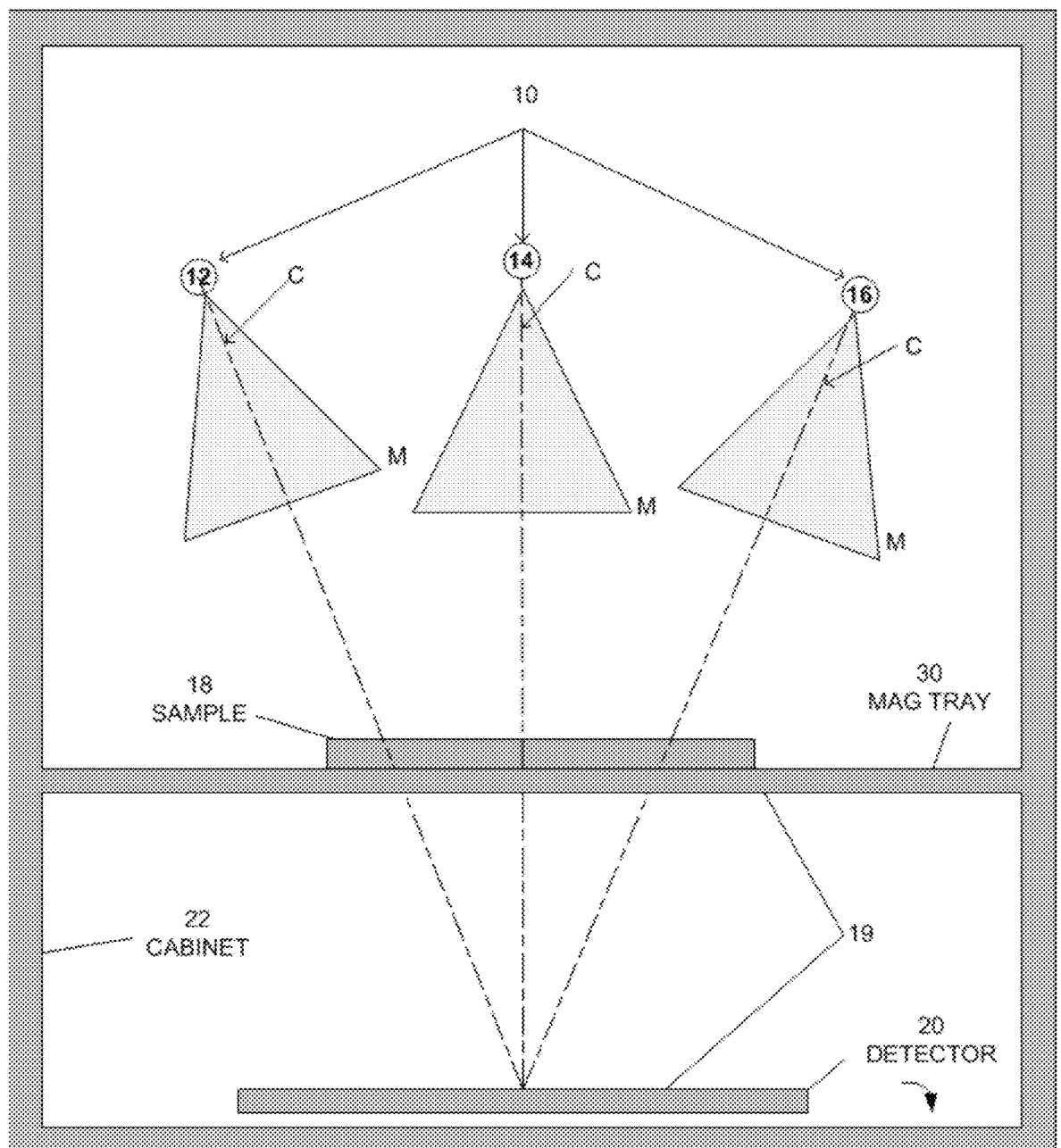
FIG. 9—Displays FIG. 1 but with the sample geometrically magnified on a raised sample tray in one embodiment of a system incorporating aspects of the present disclosure.

FIG. 9 schematically displays items as described in FIG. 1 but the difference is that the sample is raised above the detector to effect geometric magnification with distance above the detector 19 illustrated.

Figures 10A, 10B, 10C:
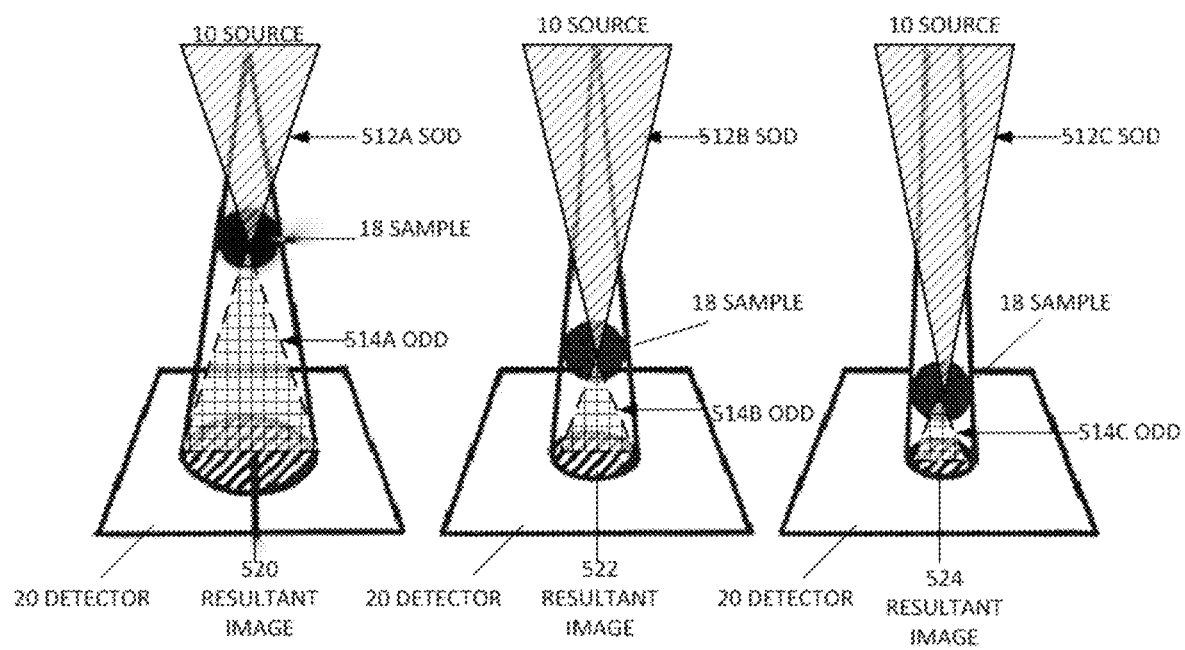
FIGS. 10A, 10B, and 10C—Display examples and theories of x-ray geometric magnification FIGS. 11A and 11B—Display an embodiment the system and computer components of the CAD system.

FIGS. 10A, 10B and 10C illustrate geometric magnification. Geometric magnification results from the detector being farther away from the X-ray source than the object. In this regard, the source-detector distance or SDD 510 (also called the source to image-receptor distance or SID) is a measurement of the distance between the x-ray tube 10 and the detector 20. The estimated radiographic magnification factor (ERMF) is the ratio of the source-detector distance 510 (SDD) over the source-object distance 512 (SOD). The source-detector distance 510 (SDD) is roughly related to the source-object distance 512 (SOD) and the object-detector distance 514 (ODD) by the equation SOD 512+ODD 514=SDD 510.

Similar to a lens in photography, where the sample 18 is positioned relative to the source 10 and detector 20 changes magnification and field of view. Three terms are used to describe positioning: source-object distance 512 (SOD, where the object represents the sample); object-image distance 514 (OID, where the image is the detector 20); and source-image distance (SID) or source detector distance 510 (SDD). The effects of moving the sample 18 and detector 20 can be seen by the method of similar triangles. In the example as shown in FIGS. 10A, 10B and 10C as the top triangles 512A, 512B and 512C (cross hatch fill) get shorter going from FIG. 10A to FIG. 10B to FIG. 10C, the bottom triangles 514A, 514B and 514C (checker fill) get longer and the base of the triangles 526A, 526B and 526C gets wider effecting magnification on the detector 20 and the magnification of the resulting images 520, 522 and 524.

In FIG. 10B the sample 18 is moved away from the source 10 and the resultant image 520, 522, 524 goes down in size (less magnified) as the sample 18 moves closer to the detector 20. Differences in magnification are exhibited by the differing triangle lengths and the resultant image which represent the source-object distance 512 (SOD) and the object-detector distance 514 (ODD). Preferably for geometric magnification, the sample 18 is supported by a magnification tray 30 (in FIGS. 8 and 9) to be imaged.

Figure 11A:
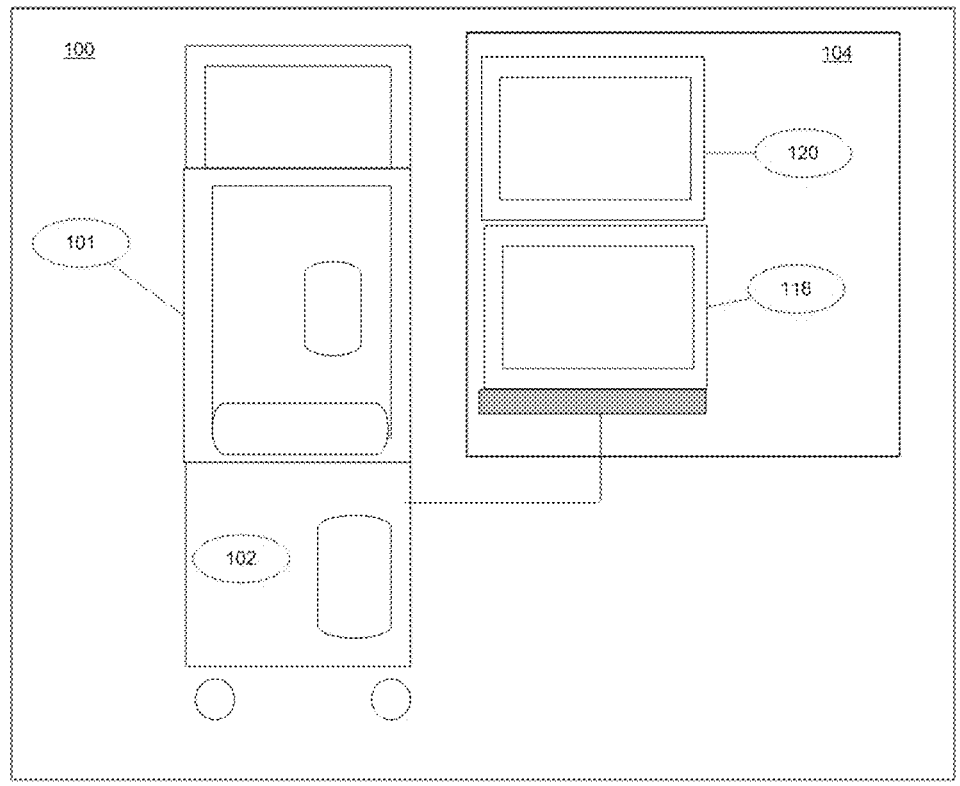
Figure 11B:
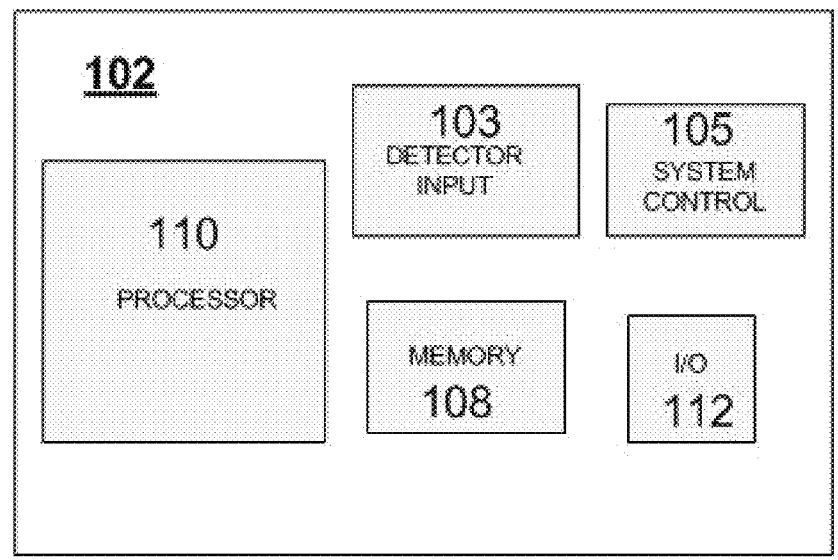

FIG. 11A shows an outside view of one embodiment of a specimen radiography system incorporating a computer aided diagnostic (CAD) system 100, for assisting in the identification of suspicious lesions in breast specimen radiograms. CAD system 100 comprises a CAD processing unit 102 and a viewing station 104. In general, CAD processing unit 102 takes the breast specimen radiograph, computes the tomosynthesis slices, and outputs a highlighted digital specimen radiogram for viewing at viewing station 104. The tomosynthesis slices can be from the same geometric magnification or more than one geometric magnification of the breast specimen. FIG. 11B shows one embodiment of a block diagram of CAD processing unit 102. CAD processing unit 102 comprises a digital detector 103 for collecting an x-ray image of a breast specimen radiogram 101, the x-ray radiogram from a tomosynthesis specimen radiographic system 100 being shown in FIG. 11A as well as previous figures and disclosure included above at an input 112 to the CAD processing unit 102. CAD processing unit 102 generally includes elements necessary for performing image processing including parallel processing steps. The tomosynthesis specimen radiogram 101 may be one of a plurality of such radiograms that can be used to produce tomosynthetic images. In particular, CAD processing unit 102 includes elements such as a central control unit 105, a memory 108, a parallel processing unit 110, and I/O (input/output) unit 112. The central control unit 105 performs the commands to manipulate the data. Memory 108 performs the temporary storage and manipulation of the data as well as storage of algorithms and other software used by the CAD system in performing aspects of the embodiments, methods and systems included herein. Parallel processing unit 110 performs and allows simultaneous calculating, and notation of all images. I/O (input/output) unit 112 performs control of the input data and the resulting output/display. It is to be appreciated that the parallel processing unit 110 shown in FIG. 11B may be replaced by a single processor without departing from the scope of the preferred embodiments. It is to be appreciated that in addition to the suspicious lesion detection algorithms disclosed herein, processing unit 102 is capable of performing a multiplicity of other image processing algorithms either serially or in parallel therewith.

Viewing station 104 is for conveniently viewing both the x-ray 2-D specimen radiogram 101 and the output of the CAD processing unit 102 on a display device 118. Viewing station 104 may also include a user interface as user interface 476 exemplified in the embodiment of FIG. 4, such as a keyboard and mouse for example. In one embodiment. Viewing station 104 can comprise a touch screen or near touch screen device separately or integrated as part of the features of display device 118 and/or $2^{nd}$ LCD monitor 120. The display device 118 may be, for example, a LCD screen. As used herein, the term "display" or "monitor" means any type of device adapted to display information, including without limitation CRTs, LCDs, TFTs, plasma displays, LEDs, and fluorescent devices. The display device 118 typically shows a highlighted digital breast specimen radiogram corresponding to the x-ray specimen radiogram 101, the highlighted digital breast specimen radiogram having information directing the attention of the radiologist to suspicious areas as determined by image processing steps performed by the CAD processing unit 102. In one preferred embodiment, the highlighted digital specimen radiogram will have black or red circles superimposed around those locations corresponding to suspicious lesions. Viewing station 104 may also comprises a $2^{nd}$ LCD monitor 120 for viewing the actual x-ray radiogram 101 itself. An alternative embodiment may include a single display device 118 in which more than one image can be displayed simultaneously. The radiologist is assisted by the CAD system 100 by viewing the display device 118, which then directs the attention of the radiologist to the suspicious portions of the actual breast specimen x-ray radiogram 101 itself.

It is to be appreciated that in addition to being able to display a single view of one breast specimen, CAD system 100 may be used in accordance with aspects of the preferred embodiments to simultaneously display information related to multiple views of the same breast specimen, for example, using both display device 118 and monitor 120, or one of the two in which more than one image is displayed, including, but not limited to, a breast specimen radiogram, tomosynthesis slices and tomosynthetic images. Thus, the attention of the radiologist may be drawn to specific areas of a first radiogram image by CAD system 100, which can then be compared to corresponding areas of other views of the same breast for making an appropriate determination as to whether a lesion is a "true lesion." A "true lesion" is a mass or dense structure that is visible in multiple views and/or slices. A suspicious lesion may be visible in one view but is not visible in another which necessitates multiple views and/or slices for confirmation as tumor-mimicking lesions show diverse etiologies and anatomic locations. Once a determination is made as to whether a lesion is "true lesion," the radiologist makes a determination if more tissue needs to be excised from the patient from whom the specimen was removed and, as a result, may expedite the closing up of the patient by highlighting more quickly and easily features that the surgeon is interested in.

Figure 12:
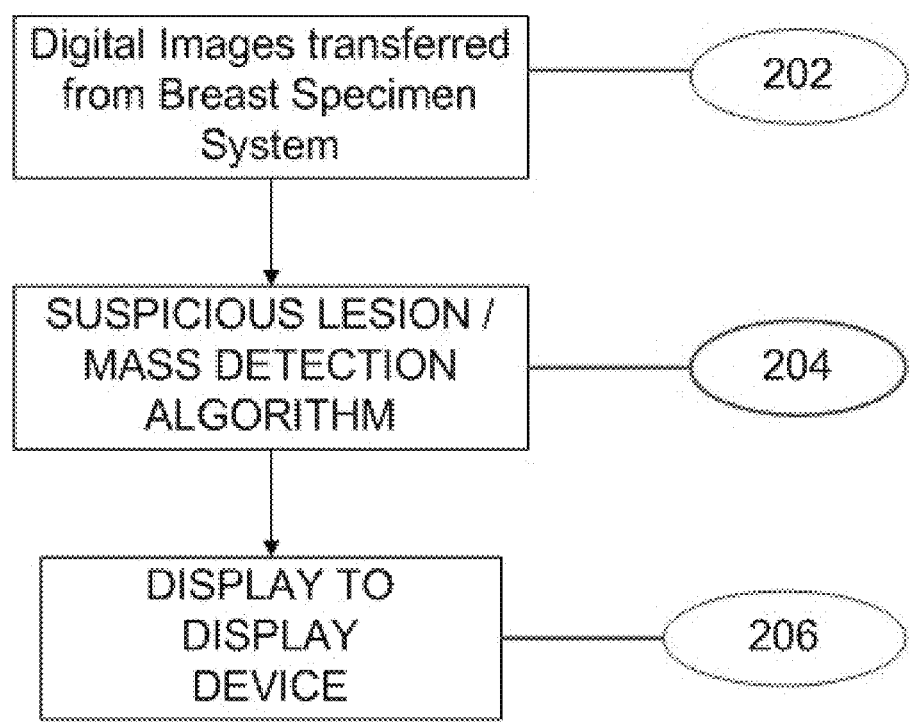
FIG. 12—Displays an embodiment of the workflow of the CAD system, process and method.

FIG. 12 shows one embodiment of the general steps performed by CAD processing unit 102 on the x-ray radiogram. At step 202, multiple related x-ray radiograms are created and transferred. To create the x-rays radiograms, the breast specimen is positioned into cabinet 101 and a plurality of images are gathered by detector input 103 and computed into multiple images/1 mm slices utilizing tomosynthesis, calculations as referred to in U.S. Pat. No. 9,138,193, Lowe, et. al., entitled "SPECIMEN RADIOGRAPHY WITH TOMOSYNTHESIS IN A CABINET" which is incorporated by reference related thereto including the systems and methods included therein. The resulting images are input and interpreted by the CAD system 100 to enable computer analysis at step 202 via radiographic images of the mass captured utilizing the detector image data 103 calculated within the computer 102 utilizing the processor 110, memory 108, and output to a monitor 104 via the i/o 112 and system control 105 for display.

Each digital breast specimen radiogram may be, for example, a 2940×2304 array of 16-bit gray scale pixel values. Such a digital breast specimen radiogram would generally correspond to a typical 14.5 cm.×11.4 cm x-ray radiogram collected at a 50 micron spatial resolution. Because a full resolution image such as the 2940×2304 image described above is not always necessary for the effectiveness of the preferred embodiments, the image may be locally averaged, using steps known in the art, down to a smaller or binned size corresponding, for example, to a 100 micron spatial resolution.

As shown in FIG. 12, the digital radiograms are processed at step 204 by an overall suspicious lesion detection algorithm in accordance with the preferred embodiments. As discussed previously, the overall lesion detection algorithms performed at step 204 generate in real-time a list of locations in at least one of the digital breast specimen radiogram images which correspond to suspicious lesions, i.e. possibly cancerous lesions. Following step 204, the digital breast specimen radiogram images and list of suspicious locations is sent in real-time for display to the viewing station 104 at step 206.

Figure 13:
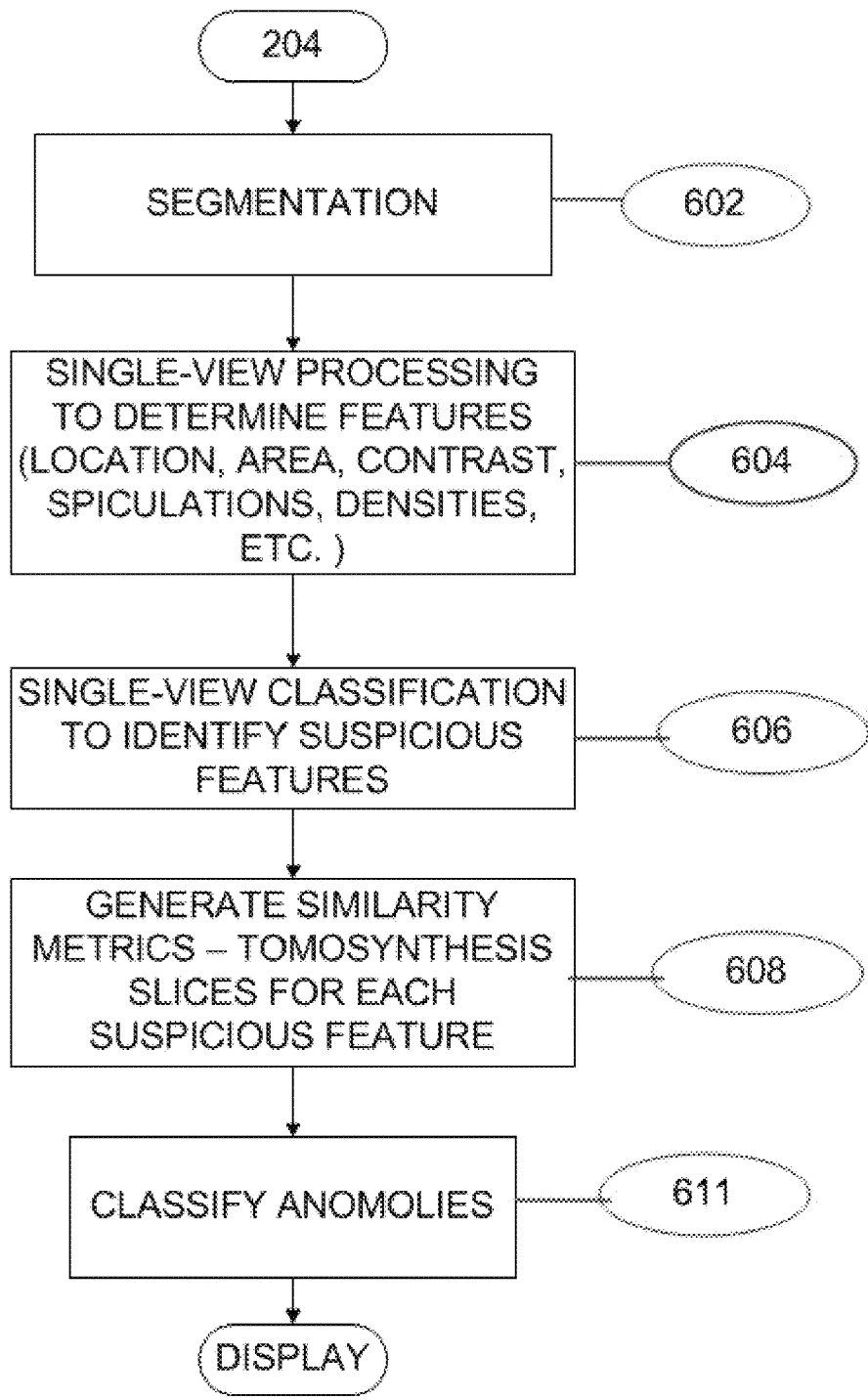
FIG. 13—Displays another embodiment workflow of the CAD system, process and method.

FIG. 13 shows one embodiment of the steps corresponding to step 204 for locating suspicious lesions in accordance with a preferred embodiment, wherein two views of the same breast are processed for identifying suspicious lesions in at least one of the views. In the example of FIG. 13, the two views processed are the slices computed at different depths, although other views of the same breast may be used in accordance with the preferred embodiments. At step 602 a segmentation algorithm is performed on each of the digital breast specimen radiogram view, i.e., multiple slices in this example. One purpose of segmentation is to specify reference locations from which positions in the breast may be indexed. Among other features, the position of the nipple, if present and so included with the breast specimen, is determined at step 602. In a preferred embodiment, locations of potentially suspicious lesions are then specified with respect to the nipple, although other positional metrics may be used as well. Importantly, location coordinates with respect to the nipple are carried across views of the same breast specimen when comparing features among the respective views.

At step 602, as an intermediate step in determining the position of the nipple, the skin line is segmented. Algorithms to locate the skin line have been described in the literature, one such method being described in U.S. Pat. No. 5,452,367 to Bick and Giger, the contents of which are hereby incorporated by reference into the present application. The nipple is expected to lie somewhere along the surface of the skin line.

Also at step 602, a number of available algorithms may be used for the purpose of determining suspicious lesions in a single digital breast specimen radiogram view including, but not limited to: U.S. Pat. No. 5,815,591 to Roehrig et. al.; U.S. Pat. No. 6,301,378 to Karssemeijer et. al. filed Jun. 3, 1997; U.S. Pat. No. 5,657,362 to Giger et al; U.S. Pat. No. 5,491,627 to Zhang et al; U.S. Pat. No. 5,537,485 to Nishikawa et al; and to Brake and Karssemeijer, Detection of Stellate Breast Abnormalities, Digital Mammography 1996, K. Doi, Mary Ellen Giger, Robert Nishikawa, R. Schmidt, eds., the contents of which are incorporated by reference into the present application. It is necessary that the chosen algorithm be designed to yield substantially correct results on "true" lesions with reasonable sensitivity and with as few spurious markers as possible. In a preferred embodiment, an area feature corresponding to the lesion area should also be computed, regardless of whether it is needed by the single-view lesion detection algorithm used. The area metric may become important in cross-view feature comparison steps, as further described infra.

The results of the single-view feature computation step 604 include a plurality of feature vectors for each digital breast specimen radiogram view. Often, depending on the single-view lesion detection algorithm chosen, there are many such feature vectors. There may be fewer feature vectors, however, if the selected single-view lesion detection algorithm is designed to discard feature vectors "on the fly" upon an on-the-spot-determination that a region or pixel will never be interesting. Although the contents of the feature vectors will vary depending on the particular single-view algorithm or algorithms used, each feature vector may contain, for example, the following features: location (e.g., the distance nipple vs specimen wall); area; contrast; spiculatedness; and eccentricity in which highlighting is dependent on numerous factors, i.e. number of pixels that the suspect is discovered as well as in how many slices/images. It is to be understood that there may be a greater number or a lesser number of elements in the feature vectors without departing from the scope of the preferred embodiments, and that the type of metrics contained in the feature vectors may also be different than in the above example.

At step 606, the single view feature vectors are processed in a classification algorithm to identify potentially suspicious lesions in the respective single-view digital breast specimen radiograms. It is to be appreciated that step 606 may be combined with step 604 in some algorithms for which feature vector computation and lesion detection take place in a single step. The classification scheme used to identify potentially suspicious lesions at step 606 in each of the digital breast specimen radiogram views may be any of a variety of classification algorithms including neural network algorithms, linear classifier algorithms, quadratic classifier algorithms, etc. Step 608 compares tomosynthesis slices computed previously to verify that the potential suspicious lesion appears in multiple slices/images confirming the legitimacy of the anomaly and classifying the anomaly in step 611 whether it is a calcification or a lesion and producing a legend and video display on the monitor 104 on the actual specimen and when the clinician clicks on the highlighted anomaly, the corresponding slices are displayed.

Figure 14A:
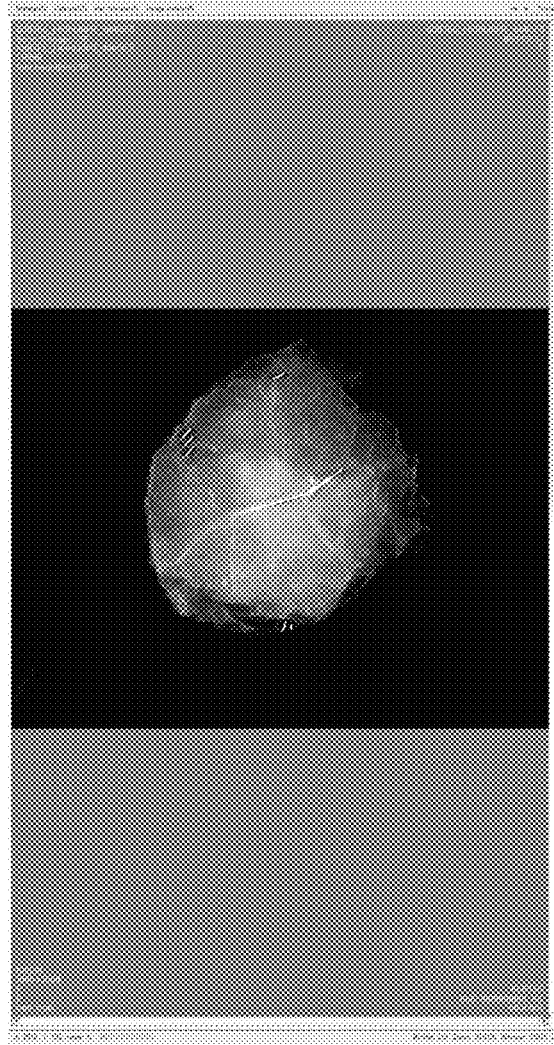
FIGS. 14a-14b—Displays a before and after picture showing the invention in operation with the highlighting of the calcifications. Whereas 14a is a basic 2-D image and 14b has color highlighting of the calcifications/lesions.
Figure 14B:
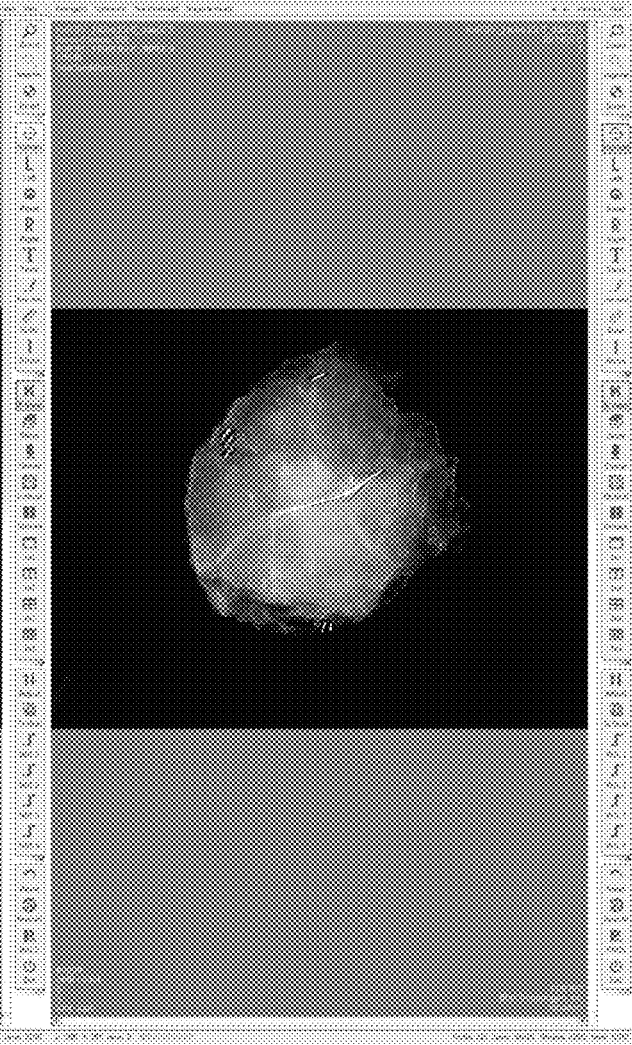

FIG. 14A displays a 2-D image of a breast specimen before applying the classification algorithm. FIG. 14B graphically displays and the color highlighting of the anomalies in green circles as computed by the classification algorithm.

Thus, while there have been shown and described and pointed out fundamental novel features of the invention as applied to the exemplary embodiments thereof, it will be understood that various omissions and substitutions and changes in the form and details of devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A real-time method for detecting suspicious lesions in a breast specimen from a patient and a medical professional identifying true lesions from suspicious lesions using information from a first digital breast specimen radiogram view of the breast specimen, a second digital breast specimen radiogram view and at least one third digital breast specimen radiogram view of the breast specimen using a cabinet x-ray system, wherein the cabinet x-ray system comprises a cabinet defining an interior chamber; an x-ray source, an x-ray detector, a specimen platform, and a motion control mechanism configured for moving the x-ray source to or along a plurality of positions within the interior chamber relative to the breast specimen disposed on the specimen platform; a display and a controller configured to selectively energize the x-ray source to emit x-rays through the breast specimen to the x-ray detector at selected positions of the x-ray source relative to the breast specimen, comprising the steps of:

removing the breast specimen from the patient and in real-time placing it on the specimen platform;

controlling the x-ray detector to generate a collection of projection x-ray images of the breast specimen when the x-ray source is energized at the selected positions such that an isocenter of the emitted x-rays at the selected positions is located at a surface of the x-ray detector, wherein one of the projection x-ray images is a two-dimensional x-ray image taken at a standard imaging angle of approximately 0°;

processing the collection of the projection x-ray images in the controller into one or more reconstructed tomosynthetic x-ray images of 1 mm slices of the breast specimen representing a volume of the breast specimen including a first reconstructed tomosynthetic x-ray image, a second reconstructed tomosynthetic x-ray image and at least one third reconstructed tomosynthetic x-ray image and relating to one or more image planes that are selectively the same or different from that of the two-dimensional x-ray image;

locating a first set of potentially suspicious lesions in said first digital breast specimen radiogram view of the breast specimen from the first reconstructed tomosynthetic x-ray image, each of said first set of potentially suspicious lesions having a first single-view feature vector corresponding thereto;

locating a second set of potentially suspicious lesions in said second digital breast specimen radiogram view of the breast specimen from the second reconstructed tomosynthetic x-ray image, each of said second set of potentially suspicious lesions having a second single-view feature vector corresponding thereto;

locating at least one third set of potentially suspicious lesions in said at least one third digital breast specimen radiogram view of the breast specimen from the at least one third reconstructed tomosynthetic x-ray image, each of said at least one third set of potentially suspicious lesions having at least one third single-view feature vector corresponding thereto;

computing a similarity metric between each of said first set of potentially suspicious lesions, each of said second set of potentially suspicious lesions and each of said at least one third set of potentially suspicious lesions using the first single-view feature vector corresponding to each of said first set of potentially suspicious lesions, the second single-view feature vector corresponding to each of said second set of potentially suspicious lesions and the at least one third second single-view feature vector corresponding to each of said at least one third set of potentially suspicious lesions;

classifying whether or not each of said first set of potentially suspicious lesions of the breast specimen is a true lesion using information from the corresponding single-view feature vector and from the corresponding similarity metrics;

displaying information for the medical professional in real-time on the display of one or more of the reconstructed tomosynthetic x-ray images having at least one potentially suspicious lesion and including information on the display identifying the position of the at least one potentially suspicious lesion and identifying if the at least one potentially suspicious lesion is a true lesion; and determining in real-time whether a second breast specimen should be removed based on the information on the display, wherein said determining step is performed by the medical professional.

2. The method of claim 1, wherein the specimen platform is a protective cover of, and in physical contact with, the x-ray detector.

3. A real-time method for detecting suspicious lesions in a breast specimen from a patient and a medical professional identifying true lesions from suspicious lesions using information from a first digital breast specimen radiogram view of the breast specimen and a second digital breast specimen radiogram view of the breast specimen using a cabinet x-ray system, wherein the cabinet x-ray system comprises a cabinet defining an interior chamber; an x-ray source, a fixed position flat panel digital x-ray detector, a specimen platform including a magnification tray that is positioned at a distance above the fixed position flat panel digital x-ray detector to facilitate geometric magnification imaging of the specimen and the breast specimen is capable of being positioned within the interior chamber at a plurality of distances above the fixed position flat panel digital x-ray detector to facilitate geometric magnification imaging of the breast specimen, and a motion control mechanism configured for moving the x-ray source to or along a plurality of positions within the interior chamber relative to the breast specimen disposed on the specimen platform; a display and a controller configured to selectively energize the x-ray source to emit x-rays through the breast specimen to the fixed position flat panel digital x-ray detector at selected positions of the x-ray source relative to the breast specimen, comprising the steps of:

removing the breast specimen from the patient and in real-time placing it on the specimen platform;

controlling the fixed position flat panel digital x-ray detector to generate a first collection of projection x-ray images of the breast specimen at a first geometric magnification when the x-ray source is energized at the selected positions such that an isocenter of the emitted x-rays at the selected positions is located at a surface of the fixed position flat panel digital x-ray detector, wherein one of the projection x-ray images is a two-dimensional x-ray image taken at a standard imaging angle of approximately 0°;

processing the first collection of the projection x-ray images at the first geometric magnification in the controller into one or more first reconstructed tomosynthetic x-ray images representing a volume of the breast specimen including a first reconstructed tomosynthetic x-ray image and relating to one or more image planes that are selectively the same or different from that of the two-dimensional x-ray image;

locating a first set of potentially suspicious lesions in said first digital breast specimen radiogram view of the breast specimen from the one or more first reconstructed tomosynthetic x-ray images, each of said first set of potentially suspicious lesions having a first single-view feature vector corresponding thereto;

changing the distance of the breast specimen on the specimen platform from the fixed position flat panel digital x-ray detector to change the geometric magnification imaging of the breast specimen;

controlling the fixed position flat panel digital x-ray detector to generate a second collection of projection x-ray images of the breast specimen at a second geometric magnification when the x-ray source is energized at the selected positions such that the isocenter of the emitted x-rays at the selected positions is located at a surface of the x-ray detector, wherein one of the projection x-ray images is a two-dimensional x-ray image taken at a standard imaging angle of approximately 0°;

processing the second collection of the projection x-ray images at the second geometric magnification in the controller into one or more second reconstructed tomosynthetic x-ray images representing a volume of the breast specimen including a second reconstructed tomosynthetic x-ray image and relating to one or more image planes that are selectively the same or different from that of the two-dimensional x-ray image at the second geometric magnification;

locating a second set of potentially suspicious lesions in said second digital breast specimen radiogram view of the breast specimen from the one or more second reconstructed tomosynthetic x-ray images, each of said second set of potentially suspicious lesions having a second single-view feature vector corresponding thereto;

computing a similarity metric between each of said first set of potentially suspicious lesions and each of said second set of potentially suspicious lesions using the first single-view feature vector corresponding to each of said first set of potentially suspicious lesions and the second single-view feature vector corresponding to each of said second set of potentially suspicious lesions;

classifying whether or not each of said first set of potentially suspicious lesions of the breast specimen is a true lesion using information from the corresponding single-view feature vector and from the corresponding similarity metrics;

displaying information for the medical professional in real-time on the display of one or more of the reconstructed tomosynthetic x-ray images having at least one potentially suspicious lesion and including information on the display identifying the position of the at least one potentially suspicious lesion and identifying if the at least one potentially suspicious lesion is a true lesion; and determining in real-time whether a second breast specimen should be removed based on the information on the display, wherein said determining step is performed by the medical professional, wherein said first digital breast specimen radiogram view is at the first geometric magnification and said second digital breast specimen radiogram view is at the second geometric magnification different from the first geometric magnification.

4. A real-time method for detecting suspicious lesions in a breast specimen from a patient and a medical professional identifying true lesions from suspicious lesions using information from a first digital breast specimen radiogram view of the breast specimen, a second digital breast specimen radiogram view and at least one third digital breast specimen radiogram view of the breast specimen using a cabinet x-ray system, wherein the cabinet x-ray system comprises a cabinet defining an interior chamber; an x-ray source, an x-ray detector, a specimen platform, and a motion control mechanism configured for moving the x-ray source to or along a plurality of positions within the interior chamber relative to the breast specimen disposed on the specimen platform; a display and a controller configured to selectively energize the x-ray source to emit x-rays through the breast specimen to the x-ray detector at selected positions of the x-ray source relative to the breast specimen, comprising the steps of:

removing the breast specimen from the patient and in real-time placing it on the specimen platform;

controlling the x-ray detector to generate a collection of projection x-ray images of the breast specimen when the x-ray source is energized at the selected positions such that an isocenter of the emitted x-rays at the selected positions is located at a surface of the x-ray detector, wherein one of the projection x-ray images is a two-dimensional x-ray image taken at a standard imaging angle of approximately 0°;

processing the collection of the projection x-ray images in the controller into one or more reconstructed tomosynthetic x-ray images of the breast specimen representing a volume of the breast specimen including a first reconstructed tomosynthetic x-ray image, a second reconstructed tomosynthetic x-ray image and at least one third reconstructed tomosynthetic x-ray image and relating to one or more image planes that are selectively the same or different from that of the two-dimensional x-ray image;

locating a first set of potentially suspicious lesions in said first digital breast specimen radiogram view of the breast specimen from the first reconstructed tomosynthetic x-ray image, each of said first set of potentially suspicious lesions having a first single-view feature vector corresponding thereto;

locating a second set of potentially suspicious lesions in said second digital breast specimen radiogram view of the breast specimen from the second reconstructed tomosynthetic x-ray image, each of said second set of potentially suspicious lesions having a second single-view feature vector corresponding thereto;

locating at least one third set of potentially suspicious lesions in said at least one third digital breast specimen radiogram view of the breast specimen from the at least one third reconstructed tomosynthetic x-ray image, each of said at least one third set of potentially suspicious lesions having at least one third single-view feature vector corresponding thereto;

computing a similarity metric between each of said first set of potentially suspicious lesions, each of said second set of potentially suspicious lesions and each of said at least one third set of potentially suspicious lesions using the first single-view feature vector corresponding to each of said first set of potentially suspicious lesions, the second single-view feature vector corresponding to each of said second set of potentially suspicious lesions and the at least one third second single-view feature vector corresponding to each of said at least one third set of potentially suspicious lesions;

classifying whether or not each of said first set of potentially suspicious lesions of the breast specimen is a true lesion using information from the corresponding single-view feature vector and from the corresponding similarity metrics;

displaying information for the medical professional in real-time on the display of one or more of the reconstructed tomosynthetic x-ray images having at least one potentially suspicious lesion and including information on the display identifying the position of the at least one potentially suspicious lesion and identifying if the at least one potentially suspicious lesion is a true lesion; and determining in real-time whether a second breast specimen should be removed based on the information on the display, wherein said determining step is performed by the medical professional.

\* \* \* \* \*